United States Patent [19]

Piantadosi et al.

[11] Patent Number: 5,614,548
[45] Date of Patent: Mar. 25, 1997

[54] QUATERNARY AMINE CONTAINING ETHER OR ESTER LIPID DERIVATIVES AND THERAPEUTIC COMPOSITIONS

[75] Inventors: Claude Piantadosi; Khalid S. Ishaq; Canio J. Marasco, Jr., all of Chapel Hill; Larry W. Daniel, Winston-Salem; Louis S. Kucera, Pfafftown; Edward J. Modest, Winston-Salem; Barry P. Goz, Chapel-Hill, all of N.C.

[73] Assignee: Wake Forest University, Winston-Salem, N.C.

[21] Appl. No.: 303,214

[22] Filed: Sep. 8, 1994

Related U.S. Application Data

[63] Continuation of Ser. No. 36,541, Mar. 22, 1993, abandoned, which is a continuation of Ser. No. 379,003, Jul. 11, 1989, abandoned, which is a continuation-in-part of Ser. No. 262,458, Oct. 25, 1988, abandoned.

[51] Int. Cl.⁶ .................... A61K 31/095; A61K 31/395; C07F 9/38; C07D 513/20; C07D 233/02

[52] U.S. Cl. .................... 514/440; 514/239.2; 514/255; 514/317; 514/336; 514/342; 514/467; 514/513; 514/547; 514/548; 514/549; 514/642; 514/643; 514/665; 514/676; 544/158; 544/177; 544/374; 544/398; 544/399; 546/248; 546/264; 546/265; 546/339; 548/203; 548/204; 548/311.1; 548/315.1; 548/341.1; 548/342.1; 548/570; 548/572; 549/30; 549/35; 549/457; 554/42; 554/43; 554/45; 560/147; 564/291; 564/292; 564/503; 564/508

[58] Field of Search ................ 514/642, 665, 514/676, 513, 547, 548, 549, 552, 643, 440; 549/30, 35, 457; 564/291, 292, 503, 508

[56] References Cited

U.S. PATENT DOCUMENTS

| | | | |
|---|---|---|---|
| 2,086,582 | 7/1937 | Taub et al. I | 564/292 X |
| 2,087,132 | 7/1937 | Taub et al. II | 564/292 |
| 2,108,765 | 2/1938 | Damagk | 514/642 X |
| 2,209,383 | 7/1940 | Bock | 564/292 X |
| 2,439,969 | 4/1948 | Fourneau, I | 549/451 |
| 2,445,393 | 7/1948 | Fourneau, II | 549/451 |
| 2,513,747 | 7/1950 | Sailmann et al. | 549/451 X |
| 2,606,909 | 8/1952 | Blicke | 549/451 |
| 2,689,790 | 9/1953 | Mowry et al. | 564/292 |
| 2,950,253 | 8/1960 | Kling et al. | 564/291 |
| 3,054,678 | 9/1962 | Michener et al. | 514/642 X |
| 3,694,473 | 9/1972 | Bibl et al. I | 564/242 X |
| 4,093,714 | 6/1978 | Tolman et al. | 424/180 |
| 4,096,278 | 6/1978 | Queille | 514/642 |
| 4,119,714 | 10/1978 | Kny et al. | 514/642 X |
| 4,159,988 | 7/1979 | Eibl et al., II | 549/451 X |
| 4,235,877 | 11/1980 | Fullerton | 424/89 |
| 4,329,302 | 5/1982 | Hanahan et al. | 564/292 X |
| 4,426,525 | 1/1984 | Hozumi et al. | 546/22 |
| 4,444,766 | 4/1984 | Bosies et al. | 424/211 |
| 4,471,113 | 9/1984 | MacCoss | 536/29 |
| 4,540,521 | 9/1985 | Garst et al. | 564/292 X |
| 4,619,917 | 10/1986 | Lee et al. | 514/642 X |
| 4,661,509 | 4/1987 | Gordon et al. | 514/642 X |
| 4,816,450 | 3/1989 | Bell et al. | 514/642 X |
| 4,826,823 | 5/1989 | Cook et al. | 514/46 |
| 4,835,263 | 5/1989 | Nguyen et al. | 536/27 |
| 4,837,023 | 6/1989 | Eibl | 424/439 |
| 4,841,039 | 6/1989 | Chu et al. | 536/29 |
| 4,880,782 | 11/1989 | Eckstein et al. | 514/45 |
| 5,034,394 | 7/1991 | Daluge | 514/261 |
| 5,138,045 | 8/1992 | Cook et al. | 536/27 |

FOREIGN PATENT DOCUMENTS

| | | | |
|---|---|---|---|
| 0094586 | 11/1983 | European Pat. Off. | 517/77 |
| 0109255 | 5/1984 | European Pat. Off. | 514/77 |
| 0142333 | 5/1985 | European Pat. Off. | 514/77 |
| 0145303 | 6/1985 | European Pat. Off. | 514/77 |
| 0146258 | 6/1985 | European Pat. Off. | 514/77 |
| 0252310 | 1/1988 | European Pat. Off. | 514/261 |
| 0335396 | 2/1989 | European Pat. Off. | 514/45 |
| 0310109 | 4/1989 | European Pat. Off. | 549/35 |
| 0348859 | 1/1990 | European Pat. Off. | 514/45 |
| 0416401 | 5/1990 | European Pat. Off. | 514/46 |
| 0434450 | 6/1991 | European Pat. Off. | 536/29 |
| 0632048 | 1/1995 | European Pat. Off. | 514/45 |
| 1561630 | 3/1967 | France | 514/77 |
| 3726945A1 | 10/1989 | Germany | 514/397 |
| 42-13841 | 8/1967 | Japan | 549/39 |
| 49-100224 | 9/1974 | Japan | 514/642 |
| 1029319 | 1/1989 | Japan | 514/261 |

(List continued on next page.)

OTHER PUBLICATIONS

Aggarwal, "Synthesis and Biological Evaluation of Prodrugs of Zidovudine," *J. Med. Chem.*, 33, 1505–1510 (1990).

Boldanova et al., "Protective effect of Phosphatidylcholine–containing Liposomes in Experimental Toxic Hepatitis", (*Vopr. Med. Khim*, 32, No. 3 (1986) *Chemical Abstracts*, 105, p. 67, Abstract No. 35587k (1986).

Chen, "Design and Synthesis of Novel Nucleoside Analogs as Potential Antiviral Agents," Abstract *American Assoc. of Pharmaceutical Scientists*, Orlando FL., (1993).

Crumpton, "Novel Lipid Analogs with Cytostatic and Cytocidal Activity," Submitted to *Anticancer Res.*, vol. 8, No. 6, pp. 1361–1366 (Nov.–Dec. 1988).

(List continued on next page.)

*Primary Examiner*—Floyd D. Higel
*Attorney, Agent, or Firm*—Schwegman, Lundberg, Woessner & Kluth

[57] ABSTRACT

Quaternary amine-containing ether lipid analogs of the formula $$R_1-X-R_2-N^+(R_3)(R_4)(R_5) Z^-$$

are disclosed. $R_1$ represents a hydrophobic group and $R_2$ represents the backbone of the molecule, with the quaternary amine being linked directly to the backbone. Pharmaceutical compositions including these compounds and methods of combating tumors with these compounds are disclosed. Also disclosed is a method of combating viral infections with both these compounds and ET-18-OMe and its analogs.

40 Claims, No Drawings

FOREIGN PATENT DOCUMENTS

| | | | |
|---|---|---|---|
| 90/15601 | 12/1990 | WIPO | 424/180 |
| 90/05736 | 3/1991 | WIPO | 514/45 |
| 91/05558 | 5/1991 | WIPO | 514/281 |
| 91/09602 | 7/1991 | WIPO | 514/261 |
| 91/18914 | 12/1991 | WIPO | 514/45 |
| 92/03462 | 3/1992 | WIPO | 514/45 |
| 93/08807 | 5/1993 | WIPO | 514/45 |
| 93/16092 | 8/1993 | WIPO | 514/45 |
| 93/16091 | 8/1993 | WIPO | 514/45 |
| 93/17020 | 9/1993 | WIPO | 536/29 |

OTHER PUBLICATIONS

Daniel, "Alkyl–Linked Diglygerides Inhibit Protein Kincase C Activation by Diacylglycerols" *Biochemical & Biophysical Res. Comm.*, 151, 291–97 (Feb. 29, 1988).

Dietzfelbinger, "Cytotoxic and Purging Effects of ET–18–OCH₃ in Human Malignant Lymphoid Cell Lines in Vitro," Abstract 2472, *Proceedings of the American Assoc. for Cancer Res.*, 31, 416 (Mar. 1990).

Fields, "Human Immunodeficiency Virus Induces Phosphorylation of its Cell Surface Receptor," *Nature*, 333, 278–80 (19 May 1988).

Harada, "Infection of HTLV–III/LAV in HTLV–I–Carrying Cells MT–2 and MT–4 and Application in a Plaque Assay," *Science*, 229, 563–229 (9 Aug. 1985).

Himmelmann, "Studies on the Cross Resistance Pattern of Membrane–Toxic Lipids in Vitro," Abstract 2448, *Proceedings of the American Assoc. for Cancer Res.*, 31, 416 (Mar. 1990).

L. Hsu et al., "Synthesis of Anti–Restricted Pyrimidine Acyclic Nucleosides", *Journal of Organic Chemistry*, vol. 57, No. 12, pp. 3354–3358, (1992).

B. Kasnar et al., "Synthesis of 2',3'–Dideoxy–and 3'–Azido–2', 3'–Dideoxy–Pyridazine Nucleosides as Potential Antiviral Agents", *Nucleosides & Nucleotides*, 13(1–3), pp. 459–479, (1994).

Korba, "Use of a Standard Cell Culture Assay to Assess Activities of Nucleoside Analogs Against Hepatitis B Virus Replication" *Antiviral Res.*, 19, 55–70 (1992).

L. Krugner–Higby et al. I, "Membrane–Interactive Phospholipids Inhbiit HIV Type 1–Induced Cell Fusion and Surface gp160/gp120 Binding to Monoclonal Antibody", *Aids Research and Human Retroviruses*, vol. 11, No. 6, pp. 705–712, (1995).

Krugner–Higby et al., II "Novel Membrane Interactive Ether Lipid Analogs Inhibit HIV–1 Glycoprotein Interaction with CD4+ Cells" Abstract from *32nd Interscience Conf on Antimicrobial Agents and Chemotherapy*, Anaheim, 164, (11–14 Oct. 1992).

L. S. Kucera et al., "Activity of Triciribine and Triciribine–5'–Monophosphate Against Human Immunodeficiency Virus Types 1 and 2", *Aids Research and Human Retroviruses*, vol. 9, No. 4, pp. 307–314, (1993).

Kucera, "Effect of Membrane–Active Ether Lipid (EL) Analogues on Human Immunodefiency Virus Production Measured by Plaque Assay," *Annals of the New York Acad. of Sciences*, 546–548 (26 Dec. 1990).

Kucera, "Inhibition of Humn Immunodefieiency Virus–1 (HIV–1) by Novel Membrane Interactive Ether Lipids," Abstract No. 2470, *Proceednigs of the American Assoc. for Cancer Res.*, 31, 416 (Mar. 1990).

Kucera, "Inhibition of HIV–1 Plaque Formation by a Novel Class of Membrane–Active Ether Lipid Analogs" *International Conference on Aids* Abstract No. W.C.O.21, Jun. 4–9, 1989, p. 528.

Kucera, "Investigation on Membrane Active Ether Lipid Analogs that Alter Functional Expression of HIV–1 Induces Glycoproteins and Inhibit Pathogenis," Abstract, *Innovations in Therapy of Human Viral Diseases*, Symposium, Research Triangle Park,16, (6–9 Dec. 1992).

L. Kucera et al., "Novel Ether Lipid Analogs of Platelet Activating Factor with Anti–Hepatitis B Virus Activity", (Abstract), *ICAAC Orlando*, (1994).

Kucera, "Novel Membrane–Interactive Ether Lipid Analogs That Inhibit Infectious HIV–1 Production and Induce Defective Virus Formation," *Aids Research and Human Retroviruses*, 6, 491–501 (1990).

Marasco et al., "Synthesis and Biological Activity of Novel Quaternary Ammonium Derivatives of Alkylglycerols as Potent Inhibitors of Protein Kincase C", *Jour. of Med. Chem.*, 3 No. 3, pp. 985–992 (Mar. 1990).

Marasco et al., "The Synthesis and Biological Testing of Alkyl Glycerols as Potential Inhibitors of Protein Kinase C" *American Assoc. of Pharmaceutical Scientists* Abstract, Orlando, FL., (1993).

Marasco, Jr., "The Synthesis and Biological Activity of Novel Alkylglycerol Derivatives as Inhibitors of Protein Kinase C Activity, Neoplastic Cell Growth and HIV–1 Infectivity," *Dissertation* for Ph. D., Univ. of No. Carolina, Chapel Hill 1990.

Marasco, "The Synthesis, Biological Evaluation, and Structure Activity of Amido Phosphocholines and Related Analogs as Anti–HIV–1 Agents," *6th Conf. on Aids, San Francisco*, Abstract, (20–24 Jun. 1990).

Meyer, "In Vitro Evaluation of Phosphocholine and Quaternary Ammonium Containing Lipids as Novel Anti–HIV Agents," *J. of Med. Chem.*, 34, 1377–83 (1991).

Meyer, "Synthesis and Evaluation of Anti–HIV–1 Ether Lipids," *AAPS Meeting, Atlanta* Abstract N. MN–510, p. S–41, (22–25 Oct. 1989).

Misuya, "Strategies of Antiviral Therapy in Aids, " *Nature*, 325, 773–78 (1987).

Modest, "Antineoplastic and Antiviral Properties of Ether Lipid Analogs", *15th Intl Cancer Congress*, Abstract (16–22 Aug. 1990).

Modest, "Combination Chemotherapy Studies with Antitumor and Antiviral Ether Lipid Analogs," Abstract 2471, *Proceedings of the American Assoc. for Cancer Res.*, 31, 416 Abstract 2471 (Mar. 1990).

E. Modest et al., "Comparison of Cell Kill Induced by Two Ether Lipids in Combination with Hyperthermia", *Proceedings of the American Association for Cancer Research;* Preclinical Pharmacology Experimental Therapeutics, vol. 31, pp. 416, Abstract 2467, (Mar. 1990).

Modest, "Pharmacological Effects and Anticancer Activity of New Ether Phospholipid Analogs" *The Pharmacological Effect of Lipids, III: The Role of Lipids in carcinogenesis and Therapy,* (In Press), pp. 330–337 (1989).

Nara, "Simple, Rapid, Quantitative, Syncytium–Forming Microassay for the Detection of Human Immunodeficiency Virus Neutralizing Antibody," *Aids Res. and Human Retroviruses*, 3, 283–302 (1987).

Noseda, "In Vitro Anitproliferative Activity of Combinations of Ether Lipid Analogues and DNA–interactive Agents Against Human Tumor Cells" *Journal of Cancer Research*, 48, 1788–1791 (Apr. 1988).

Ostertag, "Induction of Endogenous Virus and of Thymidine Kinase by Bromodeoxyuridine in Cell Cultures Transformed by Friend Virus" *Proc. Nat. Acad. Sci.* USA, 71, 4980–85 (Dec. 1974).

Pacheco, "Mechanisms of Toxicity of Hepsulfam in Human Tumor Cell Lines," Abstract 2446, *Proceedings of the American Assoc. for Cancer Res.*, 31, 416 (Mar. 1990).

Piantadosi, "Synthesis and Evaluation of Novel Ether Lipid Nucleoside Conjugates for Anti–HIV–1 Activity," *J. Med. Chem.*, 34, 1408–14 (1991).

Small, "Characterization of Cells Sensitive and Resistant to ET–18–OCH," Abstract 2447, *Proceedings of the American Assoc. for Cancer Res.*, 31, 416 (Mar. 1990).

E. E. Swayze et al., "Synthesis of 1–(2–Aminopropyl) Benzimidazoles, Structurally Related to the Tibo Derivative R82150, With Activity Against Human Immunodeficiency Virus", *Bioorganic & Medical Chemistry Letters*, vol. 3, No. 4, pp. 543–546, (1993).

J. Thompson et al., "Phospholipid Analog Inhibition of Human Immunodeficiency Virus Envelope Glycoprotein–Mediated Cell Fusion", *Abstracts of the 2nd National Conference on Human Retroviruses, Session 18*, (1995).

Yanagawa, "Spontaneous Formation of Superhelical Strands," *J. Am. Chem. Soc.*, 111, 4567–70 (1989).

Yarchoan, "Therapeutic Strategies in the Treatment of Aids, " *Annual Reports in medicinal Chemistry*, 253–263 (1988).

Kucera et al, Abstracts 5th Internl Conference Aids, Montreal, p. 528 (Jun. 1989).

Lehninger, Biochemistry, 2d. Ed., pp. 290–291 (1975).

Marx et al, J. Med. Chem., vol. 31 (4), p. 858 (1988).

Morrey et al, J. Acquired Immune Deficiency Syndromes, 3:500–510 (1990).

Morris–Natschke et al., J. Med. Chem., vol. 29(10), p. 2114 (1986).

Noseda et al, Lipids, vol. 22(11), p. 878 (1987).

Sarin et al, New Engl. J. Med., vol. 313, p. 1289 (1985).

QUATERNARY AMINE CONTAINING ETHER OR ESTER LIPID DERIVATIVES AND THERAPEUTIC COMPOSITIONS

RELATED APPLICATIONS

This application is a continuation of pending prior application Ser. No. 08/036,541, filed on 22 Mar. 1993, which is a continuation application of prior application Ser. No. 07/379,003, filed on 11 Jul. 1989, which is a continuation-in-part application of prior application Ser. No. 07/262,458, filed on 25 Oct. 1988, all now abandoned, the disclosures of which are incorporated by reference herein in their entirety.

FIELD OF THE INVENTION

This invention relates to quaternary amine containing ether or ester lipid analogs, pharmaceutical compositions including the same, and methods of treatment employing the same.

BACKGROUND OF THE INVENTION

Ether lipids are the focus of considerable interest as new anti-tumor drugs. This interest has become so great that the journal *Lipids* recently devoted an entire issue to the First International Symposium on Ether Lipids in Oncology. See *Lipids* 22 (11), 775–980 (1987) (hereinafter "*Ether Lipids in Oncology*").

The model for new ether lipid anti-tumor drugs is rac-1-O-octadecyl-2-O-methyl-glycero-3-phosphocholine (ET-18-OMe), which was synthesized by Weltzein and Arnold in 1967. See *Ether Lipids in Oncology* at 787. Among numerous noteworthy subsequent developments are the sulphur-containing phospholipids described in Bosies et al. U.S. Pat. No. 4,444,766, the phosphoric acid ester derivatives of 1,3-Dioxy propane disclosed in Hozumi et al. U.S. Pat. No. 4,426,525, the cyclimmonium salts disclosed (as platelet activating factor inhibitors) in Lee et al. U.S. Pat. No. 4,619,917, and the lipoidal amine disclosed by J. Wolff et al., *Cancer Immunol. Immunother.* 12, 97, 98 (1982).

Lipids are also of interest as protein kinase C inhibitors. Pioneering work in this area is reported in Bell, Loomis, and Hannun U.S. Pat. No. 4,816,450. As noted therein, inhibition of protein kinase C is useful in a variety of ways. Such inhibition can, for example, lead to inhibition of the oxidative burst in neutrophils, whereby an anti-inflammatory effect is achieved. Inhibition of protein kinase C can also lead to inhibition of differentiation and growth of cells and can thereby, and through other mechanisms, produce an anti-tumor effect. Hence, there is continuing interest in developing new protein kinase C inhibitors.

Quaternary amine-containing derivatives of glycerol have been suggested for purposes such as surfactants for pharmaceutical formulations, See European Pat. App. No. 187, 702 (*Chem. Abstracts* 105, 178443), and as textile finishing agents, see French Pat. No. 1,561,630, but these suggestions do not relate to the use of lipids as biologically active agents.

The present invention is based on our ongoing research into the use of ether lipid analogs in oncology.

DESCRIPTION OF THE INVENTION

Disclosed herein are compounds of the formula:

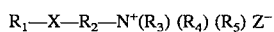

$$R_1—X—R_2—N^+(R_3)(R_4)(R_5)\ Z^-  \qquad (I)$$

and the pharmaceutically acceptable salts thereof.

Insofar as we are aware, the compounds disclosed in connection with Formula (I), and particularly the various specific compounds disclosed below, are unique as biologically active agents. In Formula (I) above, $R_2$ represents the "backbone" of the molecule. Particularly noteworthy features of the compound of Formula (I) are the hydrophobic group at $R_1$ and the quaternary amine bonded directly to the backbone as shown. We have found the activity of these compounds, as discussed in detail below, tolerant of structural changes.

In this disclosure, each variable substituent contained in parentheses is bonded to the atom to the left of the variable substituent shown in parentheses. Covalent bonds shown in the formulas are single bonds unless explained to be otherwise in the text, in which case the group or groups to be deleted in view of the double bond are identified.

In the compounds of Formula (I) above, X is S or O.

$R_1$ is linear or branched, saturated or unsaturated C10–C20 alkyl containing not more than four double bonds, linear or branched, saturated or unsaturated C10–C20 acyl containing not more than four double bonds, phenyl, or naphthyl. This alkyl or acyl may optionally be interrupted by oxygen, selenium, tellurium, phenyl, or naphthyl. For example, the interruption of an alkyl group in this position is shown in Bosies et al. U.S. Pat. No. 4,444,766. More preferably, $R_1$ is C14–C20 linear saturated or unsaturated alkyl containing not more than three double bonds. Most preferably, $R_1$ is C16–C18 linear alkyl containing not more than one double bond.

$R_2$ is C5 to C6 cycloalkylene, or a straight-chained or branched, saturated or unsaturated aliphatic hydrocarbon chain containing 2–8 carbon atoms, which is unsubstituted or substituted one or more times by hydroxyl, phenyl, C1–C5 acyloxy, C1–C5 alkylthio, C1–C5 acylated amino or by C1–C5 alkoxy which is unsubstituted or is substituted by phenyl or C1–C5 alkoxy. A carbon of $R_2$ may optionally be linked to a carbon of $R_1$ to form a ring. Preferably, $R_2$ is C2–C4 linear alkyl which is unsubstituted or is substituted one or two times by hydroxyl, phenyl, C1–C5 acyloxy, C1–C5 alkylthio, C1–C5 acylated amino or by C1–C5 alkoxy which is unsubstituted or is substituted by phenyl or C1–C5 alkoxy, with a carbon of $R_2$ optionally linked by an S or O atom to a carbon of $R_1$ to form a ring. More preferably, $R_2$ is linear C2–C4 alkyl which is unsubstituted or substituted one or two times by hydroxyl, phenyl, C1–C5 acyloxy, C1–C5 alkylthio, C1–C5 acylated amino or by C1–C5 alkoxy which is unsubstituted or is substituted by phenyl or C1–C5 alkoxy. When $R_2$ is linked to $R_1$ to form a ring, $R_2$ is preferably linked to $R_1$ by an —O— or —S— atom (e.g., 1,3 dioxolane or 1,3 dithiolane). Numerous suitable backbones ($R_2$ herein) are shown in Bosies et al. U.S. Pat. No. 4,444,766. ($R_3$ therein), the disclosure of which is to be incorporated herein by reference.

$R_3$ herein is linear or branched, saturated or unsaturated C1–C20 alkyl containing not more than four double bonds, optionally substituted with from one to three hydroxy groups (preferably, the terminal carbon is hydroxy substituted). Preferably, $R_3$ is linear or branched, saturated or unsaturated C1–C18 alkyl containing not more than three double bonds, and which is optionally substituted from one to three times by hydroxy. More preferably, $R_3$ is linear C1–C10 alkyl optionally hydroxy substituted. Most preferably, $R_1$ is linear C2–C6 alkyl, and is hydroxy substituted at the terminal carbon.

$R_4$ is hydrogen or C1–C5 alkyl. Preferably, $R_4$ is methyl, ethyl, or propyl. More preferably, $R_4$ is methyl or ethyl.

In the alternative, $R_3$ and $R_4$ are covalently joined and together with $N^+$ form a five or six membered aromatic or aliphatic monocyclic ring which may optionally contain one further hetero atom selected from oxygen, nitrogen or sulfur. This ring is optionally substituted from one to three times by hydroxy or C1–C4 alkylhydroxy. Exemplary rings are piperidine, pyridine, morpholine, pyrrolidine, piperazine, thiazole, and imidazole, which rings are optionally (but preferably) substituted from one to three times by hydroxy or C1–C4 alkylhydroxy. Prefered rings are piperidine and pyridine, which rings are optionally (but preferably) monohydroxy substituted.

$R_5$ is hydrogen or C1–C5 alkyl, except that when either $R_3$ or $R_4$ is joined to $N^+$ with a double bond, then $R_5$ is absent. Preferably, $R_5$ is methyl, ethyl, or propyl. More preferably, $R_5$ is methyl or ethyl.

$Z^-$ is an anion, such as bromine, chlorine, or iodine. $Z^-$ may or may not be a pharmaceutically acceptable anion, pharmaceutically unacceptable salts being useful for the preparation of pharmaceutically acceptable salts. Pharmaceutically acceptable salts are discussed below.

Further details of various alternate embodiments of the compounds of Formula (I) are disclosed in connection with Formulas (IIa) to (IIc) below.

Disclosed herein are compounds of the formula:

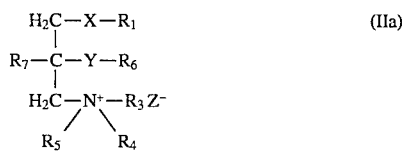

and the pharmaceutically acceptable salts thereof.

In the compounds of Formula (IIa), the embodiments and preferred embodiments of groups X, $R_1$, $R_3$, $R_4$, $R_5$, and $Z^-$ are as given in connection with Formula (I) above.

Y is S, O, or a valence bond.

$R_6$ is hydrogen or linear or branched, saturated or unsaturated C1–C20 alkyl containing not more than four double bonds or one triple bond, optionally substituted by C1–C5 alkoxy. $R_7$ is hydrogen, phenyl, or linear or branched, saturated or unsaturated C1–C16 alkyl containing not more than four double bonds or one triple bond.

Preferably, $R_6$ is hydrogen or linear or branched, saturated or unsaturated C1–C18 alkyl containing not more than two double bonds or one triple bond, optionally substituted by methoxy. More preferably, $R_6$ is hydrogen, C1–C8 or C16–C18 linear alkyl, methoxymethyl or propargyl.

Preferably, $R_7$ is H or linear or branched, saturated or unsaturated C1–C16 alkyl containing not more than three double bonds or one triple bond. More preferably, $R_1$ is H, C1–C8 alkyl, methoxymethyl or propargyl.

In a preferred embodiment of Formula (IIa), X is S or O; Y is S or O; $R_1$ is C16–C18 linear alkyl containing not more than one double bond; $R_3$ is linear C2–C6 alkyl hydroxy substituted at the distal carbon; $R_4$ is methyl or ethyl; or $R_3$ and $R_4$ are covalently joined and together with $N^+$ form a six membered heterocyclic ring selected from the class consisting of piperidine and pyridine, which ring is monohydroxy substituted; $R_5$ is methyl or ethyl, except that $R_5$ is absent when $R_3$, $R_4$, and $N^+$ form pyridine; $R_6$ is hydrogen, C1–C8 or C16–C18 linear alkyl, methoxymethyl or propargyl; and $R_7$ is H, C1–C8 linear alkyl, or propargyl.

Also disclosed herein are compounds of the formula:

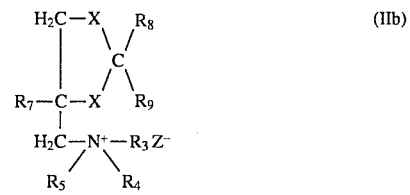

and the pharmaceutically acceptable salts thereof.

In the compounds of Formula (IIb), the embodiments and preferred embodiments of groups X, $R_3$, $R_4$, $R_5$, and $Z^-$ are as given in connection with Formula (I) above. $R_7$ is as given in connection with Formula (IIa) above.

$R_8$ is hydrogen, phenyl, or saturated or unsaturated, linear or branched C1–C19 alkyl containing not more than four double bonds. Preferably, $R_8$ is hydrogen or C1–C8 linear alkyl. More preferably, $R_8$ is hydrogen, methyl, or ethyl.

$R_9$ is phenyl or saturated or unsaturated, linear or branched C1–C19 alkyl containing not more than four double bonds. Preferably, $R_9$ is saturated or unsaturated C1–C19 linear alkyl containing not more than three double bonds. Most preferably, $R_9$ is methyl or C17 linear saturated alkyl.

Also disclosed herein are compounds of the formula:

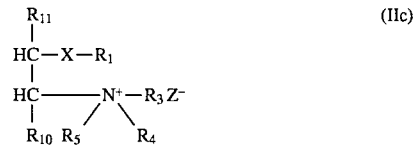

and the pharmaceutically acceptable salts thereof.

In the compounds of Formula (IIc), the embodiments and preferred embodiments of the groups X, $R_1$, $R_3$, $R_4$, $R_5$ and $Z^-$ are as given in connection with Formula (I) above. $R_{10}$ is hydrogen or methyl, preferably hydrogen. $R_{11}$ is hydrogen or methyl, preferably hydrogen.

Compounds of the Formula (I) above can be produced by known processes, preferably by the reaction of a compound of the general Formulas IIIa, IIIb or IIIc

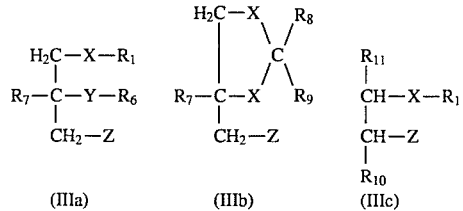

in which $R_1$, $R_6$, $R_7$, $R_8$, $R_9$, $R_{10}$, $R_{11}$, X and Y have the aforesaid meanings, and Z represents a group of the sulfonic acid ester or a halogen, with an amine of Formula (IV) below

in which $R_3$, $R_4$, and $R_5$ have the aforesaid meanings, and by subsequent conversion to pharmacologically harmless salts if necessary.

If Z represents a sulfonic acid ester, this ester is preferably methane sulfonyl, benzene sulfonyl, or p-toluenesulfonyl. The halogen should be chlorine, bromine or iodine, preferably bromine or iodine. The reactions are carried out in inert solvents, such as, for example, dimethylformamide, dimethylacetamide or acetonitrile, at temperatures between 0° C. and 100° C., preferably at 40° C.–65° C.

The compounds of the Formula (IIIa–c) which are used in the aforesaid process, can be produced from the corresponding alcohols of the general Formula (Va–c)

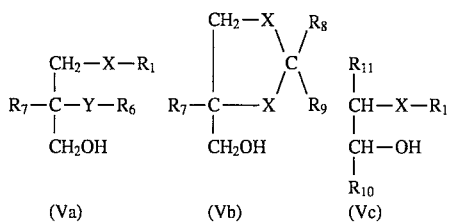

(Va)  (Vb)  (Vc)

by a reaction with a chloride of the sulfonic acid or by direct halogenation with, for example, phosphorus tribromide, phosphorus pentabromide, thionylchloride, or with triphenyl phosphine and carbon tetrabromide. Also suitable is conversion of the sulfonic acid ester by means of an alkali halogenide, such as, for example, lithium bromide and lithium chloride.

This last-mentioned reaction is preferably carried out in acetone. The halogenation with a phosphorus halogenide occurs in inert solvents, such as, for example, diethyl ether or methylene chloride in the presence of a base, such as, for example, triethylamine or pyridine, it being possible to use the pyridine simultaneously as a solvent. The reaction with a chloride of the sulfonic acid occurs under the same reactive conditions.

Compounds of the general Formulas Va–c are known from the literature (such as, for example, U.S. Pat. No. 4,444,766 or U.S. Pat. No. 4,426,525), or can be produced by the methods described therein.

In case the compounds disclosed above have an asymmetric carbon atom, the present invention also concerns the enantiomeric forms. The resolution of the racemates into the enantiomeric forms can be done in the last step of the process, or in the appropriate preceding step, by known procedures, for example, by converting the racemate with an optically active reagent into a diasteriomeric pair and subsequent resolution thereof.

The compounds disclosed in Formulas (I) and (IIa–c) above can be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine.

The compounds described above can be combined with an inert pharmaceutical carrier to provide a pharmaceutical composition for enteral or parenteral administration. The compounds described above being the active ingredient in these compositions, they should be included in an amount effective to accomplish the intended treatment (e.g., the methods of treatment herein described). For the preparation of these compositions, use can be made of pharmaceutical carriers adapted for all conventional forms of administration, for example, tablets, capsules, dragees, syrups, solutions, suspensions and the like. As injection medium, it is preferred to use water which contains the additives usual in the case of injection solutions, such as stabilizing agents, solubilizing agents and/or buffers. Additives of this kind include, for example, human serum albumin and synthetic analogs thereof, tartrate and citrate buffers, ethanol, complex formers (such as ethylenediamine-tetraacetic acid and the non-toxic salts thereof) and high molecular weight polymers (such as liquid polyethylene oxide) for viscosity regulation. Liquid carrier materials for injection solutions must be sterile and are preferably placed into ampules. Solid carrier materials include, for example, starch, lactose, mannitol, methylcellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and/or sweetening agents.

A method of combating tumors comprises administering to a subject in need of such treatment a compound as described in Formulas (I) or (IIa–c) above in an amount effective to combat the tumor(s). The term "tumors," as used herein, include both solid tumors and leukemia. The compounds of Formula (I) or (IIa–c) are particularly preferred for treating leukemia. The dosage to be administered depends upon a variety of factors, such as mode of administration, species, age, and subject condition. Usually, the dosage to be administered is from about 0.05 to about 100 milligrams per kilogram of body weight, more preferably between about 0.1 and about 75 milligrams per kilogram of body weight, and most preferably between about 0.5 and about 50 milligrams per kilogram of body weight.

The compounds described in Formulas (I) and (IIa–c) above, when administered for combating tumors, may be administered in combination with a tubulin binding agent. The tubulin binding agent should be administered in an amount effective to itself combat tumors, and preferably an amount synergistic with the compounds disclosed herein. Preferred tubulin binding agents are the vinca alkaloids and analogs thereof. See Goodman and Gilman's *The Pharmacological Basis of Therapeutics,* 1277–80 (7th ed. 1985). Particularly preferred vinca alkaloids are Vincristine, Vinblastine and Vindesine. Compounds of Formula (IIc) are preferred for use in combination with tubulin binding agents.

A method of inhibiting protein kinase C comprises contacting protein kinase C with an inhibitory amount of a compound as described in Formulas (I) or (IIa–c) above.

Protein kinase C according to the present invention includes the enzyme discussed by Nishizuka, *Science* 233, 305 (1986), which is hereby incorporated by reference herein. Functional equivalents of this enzyme (i.e., homologous proteins which have essentially the same activity as protein kinase C) which are known or are discovered are also included under the meaning of protein kinase C. For example, isozymes of protein kinase C, three of which are known, are included in the meaning of protein kinase C. This method may be carried out in vivo or in vitro. Thus, one embodiment of this method comprises administering to a mammalian subject afflicted with an inflammation a protein kinase C inhibitory amount of a compound of Formulas (I) or (IIa–c) above. Other conditions in which the activity of protein kinase C is accelerated, or which are treatable by inhibiting protein kinase C, are asthma, psoriasis, and tumor metastases. Further details on practicing methods of inhibiting protein kinase C are given in U.S. Pat. No. 4,816,450, the disclosure of which is to be incorporated herein by reference. Pharmaceutical compositions containing compounds of Formulas (I) and (IIa–c) useful for methods of inhibiting protein kinase C are prepared as described above.

A method of combating human immunodeficiency virus Type 1 (HIV-1) infection of cells comprises administering to the cells a compound as described in Formulas (I) or (IIa–c) above in an amount effective to inhibit replication of the virus in the cells. Also useful for combating viral infections in such a method are compounds of the Formula (VI) below and the pharmaceutically acceptable salts thereof:

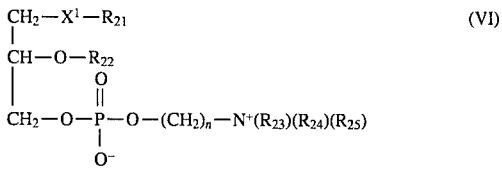

wherein:

n is 2–4. Preferably n is 2.

$X^1$ is S, O, or NHCO.

$R_{21}$ is C14–C20 linear saturated or unsaturated alkyl containing not more than three double bonds. Preferably, $R_{21}$ is C16–C18 linear alkyl containing not more than one double bond.

$R_{22}$ is hydrogen, methyl, or ethyl.

$R_{23}$, $R_{24}$, and $R_{25}$ are each independently either hydrogen or methyl, preferably methyl.

Compounds of Formula (VI) and the pharmaceutically acceptable salts thereof are useful for combating viral infections in like manner as the compounds of Formulas (I) and (IIa–c) above. To combat HIV-1 infection in a subject (e.g., a human subject) in need of such treatment, the foregoing procedure is modified so that the identified compounds are administered to the subject in an amount effective to combat the infection. Dosage ranges and mode of administration are the same as those given for the treatment of tumors above. Pharmaceutical compositions for treating HIV-1 infections are prepared as described above.

In addition to the compounds given in the examples below, the following compounds, illustrative of Formulas (I) and (IIa–c) above, can be made by following the teachings of these examples in combination with procedures known to those skilled in the art.

1. 2-hexadecanoylthio-N,N-dimethyl-N-β-hydroxyethyl-1-ethyl ammonium iodide.
2. 2-octadecanoylthio-N,N-dimethyl-N-β-hydroxyethyl-1-ethyl ammonium iodide.
3. 2-dodecylthio-N,N-dimethyl-N-β-hydroxyethyl-1-ethyl ammonium iodide.
4. 2-tetradecylthio-N,N-dimethyl-N-β-hydroxyethyl-1-ethyl ammonium iodide.
5. 2-hexadecylthio-N,N-dimethyl-N-β-hydroxyethyl-1-ethyl ammonium iodide.
6. 2-hexadecylthio-N,N-dimethyl-N-gamma-hydroxypropyl-1-ethyl ammonium iodide.
7. 2-hexadecylthio-N,N-dimethyl-N-6-hydroxybutyl-1-ethyl ammonium iodide.
8. 2-octadecylthio-N,N-dimethyl-N-β-hydroxyethyl-1-ethyl ammonium iodide.
9. 3-hexadecylthio-N,N-dimethyl-N-β-hydroxyethyl-1-propyl ammonium iodide.
10. (±)-3-octadecylthio-2-hydroxy-N,N-dimethyl-N-β-hydroxyethyl-1-propyl ammonium iodide.
11. (±)-3-hexadecylthio-2-acetoxy-N,N-dimethyl-N-β-hydroxyethyl-1-propyl ammonium iodide.
12. (±)-3-hexadecylthio-2-methoxy-N,N-dimethyl-N-β-hydroxyethyl-1-propyl ammonium iodide.
13. 3-octadecylthio-N,N-dimethyl-N-β-hydroxyethyl-1-propyl ammonium iodide.
14. (±)-N-(2-heptadecyl-1,3-dithiolan-4-yl)methyl-N,N-dimethyl-β-hydroxyethyl ammonium bromide.
15. (±)-N-(2-heptadecyl-1,3-oxathiolan-4-yl)methyl-N,N-dimethyl-β-hydroxyethyl ammonium bromide.
16. (±)-N-(2-heptadecyl-1,3-oxathiolan-5-yl)methyl-N,N-dimethyl-β-hydroxyethyl ammonium bromide.
17. (±)-2-hexadecyloxy-N,N-dimethyl-N-β-hydroxyethyl-1-propyl ammonium bromide.
18. (±)-1-hexadecyloxy-N,N-dimethyl-N-β-hydroxyethyl-2-propyl ammonium bromide.
19. (±)-2-hexadecylthio-N,N-dimethyl-N-β-hydroxyethyl-1-propyl ammonium bromide.
20. (±)-1-hexadecylthio-N,N-dimethyl-N-β-hydroxyethyl-2-propyl ammonium bromide.

The quaternary amines in compounds such as 1–20 above can be replaced with a quaternary amine such as pyridinium; N-methyl, 4'-hydroxypiperidinium; N-methyl morpholinium; N-methyl pyrrolidinium; N-methyl piperazinium; thiazolium; and 3-methyl imidazolium. Exemplary of such compounds are:

21. 1-(2-octadecyloxyethyl)pyridinium iodide.
22. (±)-1-(3-octadecyloxy-2-hydroxypropyl)pyridinium iodide.
23. (±)-1-(3-hexadecyloxy-2-acetoxypropyl)pyridinium iodide.
24. (±)-1-(3-hexadecyloxy-2-methoxypropyl)pyridinium iodide.
25. 1-(3-octadecyloxypropyl)pyridinium iodide.
26. 1-(2-hexadecanoylthioethyl)pyridinium iodide.
27. 1-(2-octadecanoylthioethyl)pyridinium iodide.
28. 1-(2-tetradecylthioethyl)pyridinium iodide.
29. 1-(2-hexadecylthioethyl)pyridinium iodide.
30. (±)-1-(3-octadecylthio-2-hydroxypropyl)pyridinium iodide.
31. (±)-1-(3-hexadecylthio-2-acetoxypropyl)pyridinium iodide.
32. (±)-1-(3-hexadecylthio-2-methoxypropyl)pyridinium iodide.
33. 1-(3-octadecylthiopropyl)pyridinium iodide.
34. (±)-1-[(2-heptadecyl-1,3-dithiolan-4-yl)methyl]pyridinium bromide.
35. (±)-1-[(2-heptadecyl-1,3-oxathiolan-4-yl)methyl]pyridinium bromide.
36. (±)-1-[(2-heptadecyl-1,3-oxathiolan-5-yl)methyl]pyridinium bromide.
37. (±)-1-[2-(hexadecyloxy)propyl]pyridinium bromide.
38. (±)-1-(1-methyl-2-hexadecyloxyethyl)pyridinium bromide.
39. (±)-1-[2-(hexadecylthio)propyl]pyridinium bromide.
40. (±)-1-[1-methyl-2-hexadecyloxyethyl]pyridinium bromide.
41. 4-methyl-4-[2-(octadecyloxy)ethyl]morpholinium iodide.
42. (±)-4-methyl-4-[3-hexadecyloxy-2-hydroxypropyl] morpholinium iodide.
43. (±)-4-methyl-4-[3-hexadecyloxy-2-acetoxypropyl] morpholinium iodide.
44. (±)-4-methyl-4-[3-hexadecyloxy-2-methoxypropyl] morpholinium iodide.
45. 4-methyl-4-[3-octadecyloxypropyl]morpholinium iodide.
46. 4-methyl-4-[2-hexadecanoylthioethyl]morpholinium iodide.
47. 4-methyl-4-[2-octadecanoylthioethyl]morpholinium iodide.

48. 4-methyl-4-[2-tetradecylthioethyl]morpholinium iodide.
49. 4-methyl-4-[2-hexadecylthioethyl]morpholinium iodide.
50. (±)-4-methyl-4-[3-octadecylthio-2-hydroxypropyl] morpholinium iodide.
51. (±)-4-methyl-4-[3-hexadecylthio-2-acetoxypropyl] morpholinium iodide.
52. (±)-4-methyl-4-[3-hexadecylthio-2-methoxypropyl] morpholinium iodide.
53. 4-methyl-4-[3-octadecylthiopropyl]morpholinium iodide.
54. (±)-4-methyl-4-[(2-heptadecyl-1,3-dithiolan-4-yl)methyl]morpholinium bromide.
55. (±)-4-methyl-4-[(2-heptadecyl-1,3-oxathiolan-4-yl)methyl]morpholinium bromide.
56 (±)-4-methyl-4-[(2-heptadecyl-1,3-oxathiolan-5-yl)methyl]morpholinium bromide.
57. (±)-4-methyl-4-[2-(hexadecyloxy)propyl]morpholinium bromide.
58. (±)-4-methyl-4-[(1-methyl-2-hexadecyloxy)ethyl] morpholinium bromide.
59. (±)-4-methyl-4-[2-(hexadecylthio)propyl]morpholinium bromide.
60. (±)-4-methyl-4-(1-methyl-2-hexadecylthioethyl)morpholinium bromide.
61. 1-[2-(octadecyloxy)ethyl]-1-methyl pyrrolidinium iodide.
62. (±)-1-(3-octadecyloxy-2-hydroxypropyl)-1-methyl pyrrolidinium iodide.
63. (±)-1-(3-hexadecyloxy-2-acetoxypropyl)-1-methyl pyrrolidinium iodide.
64. (±)-1-(3-hexadecyloxy-2-methoxypropyl)-1-methyl pyrrolidinium iodide.
65. 1-(3-octadecyloxypropyl)-1-methyl pyrrolidinium iodide.
66. 1-(2-hexadecanoylthioethyl)-1-methyl pyrrolidinium iodide.
67. 1-(2-octadecanoylthioethyl)-1-methyl pyrrolidinium iodide.
68. 1-(2-tetradecylthioethyl)-1-methyl pyrrolidinium iodide.
69. 1-(2-hexadecylthioethyl)-1-methyl pyrrolidinium iodide.
70. (±)-1-(3-hexadecylthio-2-hydroxypropyl)-1-methyl pyrrolidinium.
71. (±)-1-(3-hexadecylthio-2-acetoxypropyl)-1-methyl pyrrolidinium iodide.
72. (±)-1-(3-hexadecylthio-2-methoxypropyl)-1-methyl pyrrolidinium iodide.
73. 1-(3-octadecylthiopropyl)-1-methyl pyrrolidinium iodide.
74. (±)-1-[(2-heptadecyl-1,3-dithiolan-4-yl)methyl]-1-methyl pyrrolidinium bromide.
75. (±)-1-[(2-heptadecyl-1,3-oxathiolan-4-yl)methyl]-1-methyl pyrrolidinium bromide.
76. (±)-1-[(2-heptadecyl-1,3-oxathiolan-5-yl)methyl]-1-methyl pyrrolidinium bromide.
77. (±)-1-(2-hexadecyloxypropyl)-1-methyl pyrrolidinium bromide.
78. (±)-1-(1-methyl-2-hexadecyloxyethyl)-1-methyl pyrrolidinium bromide.
79. (±)-1-(2-hexadecylthiopropyl)-1-methyl pyrrolidinium bromide.
80. (±)-1-(1-methyl-2-hexadecylthioethyl)-1-methyl pyrrolidinium.
81. 1-(2-octadecyloxyethyl)-1-methyl piperazinium iodide.
82. (±)-1-(3-octadecyloxy-2-hydroxypropyl)-1-methyl piperazinium iodide.
83. (±)-1-(3-hexadecyloxy-2-acetoxypropyl)-1-methyl piperazinium iodide.
84. (±)-1-(3-hexadecyloxy-2-methoxypropyl)-1-methyl piperazinium iodide.
85. 1-(3-octadecyloxypropyl)-1-methyl piperazinium iodide.
86. 1-(2-hexadecanoylthioethyl)-1-methyl piperazinium iodide.
87. 1-(2-octadecanoylthioethyl)-1-methyl piperazinium iodide.
88. 1-(2-tetradecylthioethyl)-1-methyl piperazinium iodide.
89. 1-(2-hexadecylthioethyl)-1-methyl piperazinium iodide.
90. (±)-1- (3-octadecylthio-2-hydroxypropyl)-1-methyl piperazinium iodide.
91. (±)-1-(3-hexadecylthio-2-acetoxypropyl)-1-methyl piperazinium iodide.
92. (±)-1-(3-hexadecylthio-2-methoxypropyl)-1-methyl piperazinium iodide.
93. 1-(3-octadecylthiopropyl)-1-methyl piperazinium iodide.
94. (±)-1-[(2-heptadecyl-1,3-dithiolan-4-yl)methyl]-1-methyl piperazinium bromide.
95. (±)-1-[(2-heptadecyl-1,3-oxathiolan-4-yl)methyl]-1-methyl piperazinium bromide.
96. (±)-1-[(2-heptadecyl-1,3-oxathiolan-5-yl)methyl]-1-methyl piperazinium bromide.
97. (±)-1-(2-hexadecyloxypropyl)-1-methyl piperazinium bromide.
98. (±)-1-(1-methyl-2-hexadecyloxyethyl)-1-methyl piperazinium bromide.
99. (±)-1-(2-hexadecylthiopropyl)-1-methyl piperazinium bromide.
100. (±)-1-(1-methyl-2-hexadecylthioethyl)-1-methyl piperazium bromide.
101. 3-(2-octadecyloxyethyl) thiazolium iodide.
102. (±)-3-(3-octadecyloxy-2-hydroxypropyl)thiazolium iodide.
103. (±)-3-(3-hexadecyloxy-2-acetoxypropyl)thiazoliumiodide.
104. (±)-3-(3-hexadecyloxy-2-methoxypropyl)thiazolium iodide.
105. 3-(3-octadecyloxypropyl)thiazolium iodide.
106. 3-(2-hexadecanoylthioethyl)thiazolium iodide.
107. 3-(2-octadecanoylthioethyl)thiazolium iodide.
108. 3-(2-tetradecylthioethyl)thiazolium iodide.
109. 3-(2-hexadecylthioethyl)thiazolium iodide.
110. (±)-3-(3-octadecylthio-2-hydroxypropyl)thiazolium iodide.
111. (±)-3-(3-octadecylthio-2-acetoxypropyl)thiazolium iodide.
112. (±)-3-(3-hexadecylthio-2-methoxypropyl)thiazolium iodide.
113. 3-(3-octadecylthiopropyl)thiazolium iodide.
114. (±)-3-[(2-heptadecyl-1,3-dithiolan-4-yl)methyl]thiazolium bromide.
115. (±)-3-[(2-heptadecyl-1,3-oxathiolan-4-yl)methyl] thiazolium bromide.
116. (±)-3-[(2-heptadecyl-1,3-oxathiolan-5-yl)methyl] thiazolium bromide.
117. (±)-3-(2-hexadecyloxypropyl)thiazolium bromide.
118. (±)-3-(1-methyl-2-hexadecyloxyethyl)thiazolium bromide.
119. (±)-3-(2-hexadecylthiopropyl)thiazolium bromide.

120. (±)-3-(1-methyl-2-hexadecylthioethyl)thiazolium bromide.
121. 1-(2-octadecyloxyethyl)-3-methyl imidazolium iodide.
122. (±)-1-(3-hexadecyloxy-2-methoxypropyl)-3-methyl imidazolium iodide.
123. (±)-1-(3-hexadecyloxy-2-acetoxypropyl)-3-methyl imidazolium iodide.
124. (±)-1-(3-hexadecyloxy-2-methoxypropyl)-3-methyl imidazolium iodide.
125. 1-(3-octadecyloxypropyl)-3-methyl imidazolium iodide.
126. 1-(2-hexadecanoylthioethyl)-3-methyl imidazolium iodide.
127. 1-(2-octadecanoylthioethyl)-3-methyl imidazolium iodide.
128. 1-(2-tetradecylthioethyl)-3-methyl imidazolium iodide.
129. 1-(2-hexadecylthioethyl)-3-methyl imidazolium iodide.
130. (±)-1-(3-octadecylthio-2-hydroxypropyl)-3-methyl imidazolium iodide.
131. (±)-1-(3-octadecylthio-2-acetoxypropyl)-3-methyl imidazolium iodide.
132. (±)-1-(3-octadecylthio-2-methoxypropyl)-3-methyl imidazolium iodide.
133. 1-(3-octadecylthiopropyl)-3-methyl imidazolium iodide.
134. (±)-1-[(2-heptadecyl-1,3-dithiolan-4-yl)methyl]-3-methyl imidazolium bromide.
135. (±)-1-[(2-heptadecyl-1,3-oxathiolan-4-yl)methyl]-3-methyl imidazolium bromide.
136. (±)-1-[(2-heptadecyl-1,3-oxathiolan-5-yl)methyl]-3-methyl imidazolium bromide.
137. (±)-1-(2-hexadecyloxypropyl)-3-methyl imidazolium bromide.
138. (±)-1-(1-methyl-2-hexadecyloxyethyl)-3-methyl imidazolium bromide.
139. (±)-1-(2-hexadecylthiopropyl)-3-methyl imidazolium bromide.
140. (±)-1-(1-methyl-2-hexadecylthioethyl)-3-methyl imidazolium bromide.
141. (±)-3-hexadecylthio-2-(methoxymethyl)-N,N-dimethyl-N-gamma-hydroxypropyl-1-propyl ammonium bromide.
142. (±)-3-octadecylthio-2-propargyl-N,N-dimethyl-N-gamma-hydroxypropyl-1-propyl ammonium bromide.

In Examples 1-24 below, proton nuclear magnetic resonance spectra were recorded in CDCl$_3$ on either a JEOLCO 60-MHz, VARIAN 80-MHz, or VARIAN 400-MHz spectrometer. Chemical shifts are reported in parts per million relative to internal tetramethylsilane. Infrared spectra were recorded on a Perkin-Elmer 1320 spectrometer as thin films. Melting points were determined on a Thomas-Hoover capillary melting point apparatus and are uncorrected. Microanalyses were performed by Atlantic Microlab Inc. All reactions were performed under a positive pressure of dry nitrogen with dry solvents. Tetrahydrofuran (THF) was distilled from Na and benzophenone, dichloromethane (DCM) from phosphorous pentoxide, triethylamine (Et$_3$N) from KOH, acetonitrile (CH$_3$CN) from calcium hydride and dimethylformamide (DMF) was placed over potassium hydroxide one week before use. Chromatographic purification was performed using silica gel 60 (230-400 mesh). Thin layer chromatographic plates were visualized either by iodine vapor or charring following sulfuric acid spray.

EXAMPLE 1

(±)-1-S-hexadecylthioglycerol

To a stirred solution of 40.0 grams (0.037 mole) 3-mercapto-1,2-propanediol in 300 milliliters of 95% ethanol, 24.9 grams (0.44 mole) of KOH was added under an inert atmosphere of nitrogen. Then, a solution of 135.0 grams (0.44 mole) bromohexadecane in 100 milliliters of 95% ethanol was added dropwise over a one-hour period, and the reaction allowed to proceed at room temperature with vigorous stirring for 24 hours. The precipitate was filtered, taken up in one liter of boiling methanol and cooled to 0° Centigrade for twelve hours. The precipitate was filtered and allowed to air dry, producing 117 grams (95%) of product (mp 72°-74° Centigrade).

EXAMPLE 2

(±)-1-O-(1'-Naphthyl)-glycerol

Into a three-neck 500 milliliter round bottom flask equipped with a reflux condenser, stir bar and a nitrogen inlet, 60 milliliters of DMF and 2.5 grams (0.083 mole) of 80% NaH (oil dispersion) were added. A solution of 6.0 grams (0.042 mole) 1-naphthol in 70 milliliters of DMF was added to the slurry over a period of 30 minutes. The reaction mixture was then heated at a gentle reflux for one hour, followed by the slow addition of 10.7 grams (0.051 mole) of (±)-1,2-isopropylidene-3-O-mesylglycerol in 45 milliliters of DMF. Heating and stirring was continued for five hours. The reaction mixture was then cooled to 0° Centigrade before 1 milliliter of water was added and the reaction mixture was filtered. The filtrate was diluted with 200 milliliters of ether and extracted once with 150 milliliters of water. The nonaqueous layer was dried over anhydrous sodium sulfate, filtered and concentrated in vacuo. Purification of the residue by silica gel chromatography (hexane:ethyl acetate 10:1 as eluent) provided 7.8 grams of a clear oil. This oil was transferred to a 250 milliliter round bottom flask equipped with a reflux condenser and stir bar, and a solution of 3 milliliters of concentrated HCl in 100 milliliters of methanol was added. The reaction mixture was refluxed for 12 hours, the solvent was removed in vacuo, and the residue dissolved in 100 milliliters of ether. The organic layer was extracted once with 100 milliliters of water, and the water layer was back extracted twice with 50 milliliter portions of ether. The ether layers were combined, dried over anhydrous sodium sulfate, filtered and the solvent removed in vacuo to yield a solid. Recrystallization from hexanes and ethyl acetate provided 5.5 grams (60.5% based on 1-naphthol) of the pure diol (±)-1-O-(1-Naphthyl)glycerol, (mp 93°-95.5° Centigrade). $^1$H-NMR (CDCl$_3$): delta, 2.5(bs, 2H, 2 OH), 3.7-4.25(m, 5H, OCH$_2$CHCH$_2$O), 6.76-6.95 (m, 1H, Naph), 7.35-7.6 (m, 4H, Naph), 7.7-7.95 (m, 1H, Naph), 8.1-8.3 (m, 1H, Naph).

EXAMPLE 3

(±)-1-S-hexadecyl-3-O-tritylthioglycerol

To a round bottom flask equipped with a magnetic stir bar and drying tube, a solution of 70 grams (0.2 mole) (±)-1-S-hexadecylthioglycerol in 300 milliliters of pyridine was added, followed by the addition of 76.0 grams (0.27 mole) triphenylmethyl chloride. The reaction mixture was stirred at room temperature. After 36 hours, the pyridine was removed in vacuo and the resulting oil was dissolved in 450 milliliters of CHCl$_3$. The solution was extracted twice with 500 milliliter portions of 5% HCl, twice with 500 milliliter portions of water and the nonaqueous solution was dried over anhydrous sodium sulfate. The drying agent was filtered, the solvent was removed in vacuo, the residue was dissolved in 500 milliliters of hexanes, and the solution was placed at −5° Centigrade for 24 hours. The resulting precipitate was redissolved in 500 milliliters of acetone and reprecipitated as before. The final precipitate was filtered and dried under vacuum to give 113 grams (94%) of product, (mp 61°–62° Centigrade). $^1$H-NMR (CDCl$_3$): delta, 0.7–1.7 [m, 31H, (C$\underline{H}_2$)$_{14}$C$\underline{H}_3$], 2.3–2.8(m, 4H, C$\underline{H}_2$—S—C$\underline{H}_2$), 3.25[d, 2H, C$\underline{H}_2$—O—C(C$_6$H$_5$)$_3$], 3.6–4.0(m, 1H, CH$_2$—C$\underline{H}$—CH$_2$), 7.0–7.6[m, 15H, C(C$_6$$\underline{H}_5$)$_3$].

EXAMPLE 4

(+)-1-O-(1'-Naphthyl)-3-O-tritylglycerol

Into a 200 milliliter round bottom flask equipped with a reflux condenser, stir bar and nitrogen inlet, was added a solution of 5.4 grams (0.025 mole) (±)-1-O-(1'-Naphthyl)-glycerol, 50 milliliters of DCM and ten milliliters of triethylamine. A solution of 8.3 grams (0.029 mole) triphenylmethyl chloride in DCM was added followed by 0.1 gram of dimethylaminopyridine. The reaction mixture was stirred overnight at room temperature. The reaction mixture was extracted with two 50 milliliter portions of water, 5% HCl (until slightly acidic), and finally with water. The organic layer was dried over anhydrous sodium sulfate, filtered and concentrated to yield a viscous oil. Purification by silica gel chromatography eluting with a discontinuous gradient of 12:1 to 5:1 hexanes: ethyl acetate provided 8.5 grams (75%) of the ether (+)-1-O-(1'-Naphthyl)-3-O-tritylglycerol). $^1$H-NMR (CDCl$_3$): delta, 2.5(bs, 2H, 2 OH), 3.5 [d, 2H, C$\underline{H}_2$—O—(C$_6$H$_5$)$_3$], 4.3(m, 3H, OC$\underline{H}_2$C$\underline{H}$CH$_2$O), 6.8–6.9(m, 1H, Naph), 7.15–7.65[m, 19H, Naph, C(C$_6$$\underline{H}_5$)$_3$], 7.7–7.95(m, 1H, Naph), 8.1–8.3(m, 1H, Naph).

EXAMPLE 5

(±)-1-S-hexadecyl-2-O-methyl-3-O-tritylthioglycerol

A solution of 6.0 grams (0.01 mole) (±)-1-S-hexadecyl-3-O-tritylthioglycerol in 250 milliliters of THF was added to a slurry of 0.4 grams (0.014 mole) 80% NaH (oil dispersion) in 50 milliliters of THF and the reaction mixture stirred at room temperature for one hour. Then 1.4 gram (0.13 mole) of CH$_3$I was added and the reaction allowed to proceed at room temperature for 24 hours. The reaction mixture was then diluted with 300 milliliters of distilled water and extracted twice with 200 milliliter portions of ether. The nonaqueous extracts were combined, dried over anhydrous sodium sulfate, filtered and removed in vacuo to provide 6.0 grams of crude product as an oil. $^1$H-NMR (CDCl$_3$): delta, 0.7–1.7[m, 31H, (C$\underline{H}_2$)$_{14}$C$\underline{H}_3$], 2.3–2.8(m, 4H, C$\underline{H}_2$—S—C$\underline{H}_2$), 3.25(m, 5H, C$\underline{H}_3$O, CH—C$\underline{H}_2$—O), 3.6–4.0(m, 1H, C$\underline{H}$), 7.6–7.0[m, 15H, C(C$_6$$\underline{H}_5$)$_3$].

EXAMPLE 6

(±)-1-S-hexadecyl-2-O-ethyl-3-O-tritylthioglycerol

This compound was prepared in an analogous manner to that of (±)-1-S-hexadecyl-2-O-methyl-3-O-tritylthioglycerol from 10.0 grams (0.02 mole) of (±)-1-S-hexadecyl-3-O-tritylthioglycerol and 3.3 grams (0.03 mole) of CH$_3$CH$_2$I to provide 10.0 grams of crude product as an oil. $^1$H-NMR (CDCl$_3$): delta, 0.7–1.7[m, 34H, (C$\underline{H}_2$)$_{14}$C$\underline{H}_3$, C$\underline{H}_3$—CH$_2$—O], 2.3–2.8(m, 4H, C$\underline{H}_2$—S—C$\underline{H}_2$), 3.5–3.9 [m, 5H, OC$\underline{H}_2$—CH$_3$, C$\underline{H}$C$\underline{H}_2$O], 7.1–7.5 [m, 15H, C(C$_6$$\underline{H}_5$)$_3$].

EXAMPLE 7

(±)-1-S-hexadecyl-2-O-methylthioglycerol

To a solution of 6.0 grams (0.01 mole) of (±)-1-S-hexadecyl-2-O-methyl-3-O-tritylthioglycerol in 100 milliliters of chloroform:methanol (3:1) was added 0.2 gram of p-toleunesulfonic acid and the reaction stirred at room temperature for 24 hours. The reaction mixture was neutralized with 1.0 gram of sodium bicarbonate and then extracted three times with 200 milliliter portions of water. The nonaqueous layer was separated and the solvent removed in vacuo to give the crude product as an oil. Silica gel chromatography (CHCl$_3$ eluent) provided 3.1 grams (89%) of pure product as a semi-waxy solid. $^1$H-NMR (CDCl$_3$): delta, 0.87(t, 3H, terminal methyl), 1.2–1.6[m, 28H, (C$\underline{H}_2$)$_{14}$], 2.58 (m, 2H, —S—C$\underline{H}_2$), 2.62 (m, 2H, CH—C$\underline{H}_2$—S—), 3.40(m, 1H, C$\underline{H}$), 3.44(s, 3H, C$\underline{H}_3$—O—), 3.75(m, 2H, C$\underline{H}_2$—OH).

EXAMPLE 8

(±)-1-S-hexadecyl-2-O-ethylthioglycerol

This compound was prepared in an analogous manner to that of (±)-1-S-hexadecyl-2-O-methylthioglycerol from 10.0 grams (0.02 mole) of (±)-1-2-hexadecyl-2-O-ethyl-3-O-tritylthioglycerol and 0.2 gram of p-toluenesulfonic acid. Silica gel chromatography (CHCl$_3$ eluent) provided 5.8 grams (95%) of a semi-waxy solid. $^1$H-NMR (CDCl$_3$): delta, 0.87(t, 3H, terminal methyl), 1.2–1.6[m, 31H, (C$\underline{H}_2$)$_{14}$, C$\underline{H}_3$—CH$_2$—O—], 2.58 (m, 2H, S—C$\underline{H}_2$), 2.62 (m, 2H, CH—C$\underline{H}_2$—S), 3.40–3.50 (m, 3H, C$\underline{H}$, CH$_3$—C$\underline{H}_2$—O), 3.75(m, 2H, C$\underline{H}_2$—OH).

EXAMPLE 9

(±)-1-O-(1'-Naphthyl)-2-O-methylglycerol

Alkylation of (+)-1-O-(1'-Naphthyl)-3-O-tritylglycerol was performed in an analogous manner to that of (±)-1-S-hexadecyl-2-O-methyl-3-O-tritylthioglycerol from 8.1 grams (0.018 mole) of (+)-1-O-(1'-Naphthyl)-3-O-tritylglycerol, 0.90 gram (0.030 mole) of 80% NaH (oil dispersion) and 2.5 milliliters (0.040 mole) of CH$_3$I to provide 8.7 grams of (±)-1-O-(1'-Naphthyl)-2-O-methyl-3-O-tritylglycerol as a glassy oil. (±)-1-O-(1'-Naphthyl)-2-O-methyl-3-O-tritylglycerol without further purification was directly deprotected using a procedure similar to that utilized for (±)-1-S-hexadecyl-2-O-methylthioglycerol. The trityl ether (±)-1-O-(1'-Naphthyl)-2-O-methyl-3-O-tritylglycerol was reacted with 1.0 gram of p-toluenesulfonic acid in 70 milliliters of a 5:2 mixture of chloroform and methanol. Purification by silica gel chromatography (elution with a discontinuous gradient of 4:1 to 1:1 of hexanes:ethyl acetate) provided 3.8 grams (92.7% based on starting compound (+)-1-O(1'-Naphthyl)-3-O-tritylglycerol) of (±)-1-O-(1'-Naphthyl)-2-O-methylglycerol. $^1$H-NMR (CDCl$_3$): delta, 2.35(bs, 1H, OH), 3.5(bs, 3H, OC$\underline{H}_3$), 3.65–3.9(m, 3H, C$\underline{H}$C$\underline{H}_2$OH), 4.13(d, 2H, CH$_2$ONaph), 6.65–6.85 (m, 1H, Naph), 7.25–7.5 (m, 4H, Naph), 7.6–7.85(m, 1H, Naph), 8.05–8.3(m, 1H, Naph).

EXAMPLE 10

(±)-1-S-hexadecyl-2-O-methyl-3-O-mesylthioglycerol

To a solution of 3.0 grams (0.009 mole) (±)-1-hexadecyl-2-O-methylthioglycerol in 200 milliliters of DCM and 1.0 milliliter (0.010 mole) of triethylamine was added 1.2 grams (0.012 mole) of methanesulfonyl chloride and the reaction stirred at room temperature for 24 hours. The reaction mixture was then extracted twice with 200 milliliter portions of water, twice with 200 milliliter portions of 5% HCl, once with 200 milliliters of saturated $NaHCO_3$, and once with 200 milliliters of brine. The organic layer was dried over anhydrous sodium sulfate, filtered and evaporated in vacuo to yield 3.4 grams (89%) of a colorless oily residue. $^1$H-NMR ($CDCl_3$): delta, 0.87(t, 3H, terminal methyl), 1.2–1.6[m, 28H, ($\underline{CH_2}$)$_{14}$], 2.58(m, 2H, S—$\underline{CH_2}$), 2.62(m, 2H, CH—$\underline{CH_2}$—S), 3.08(s, 3H, $SO_2$—$\underline{CH_3}$), 3.40–3.50(m, 4H, $\underline{CH}$, $\underline{CH_3}$—O), 4.35 (m, 2H, $\underline{CH_2}$—$OSO_2$).

EXAMPLE 11

(±)-1-S-hexadecyl-2-O-ethyl-3-O-mesylthioglycerol

This compound was prepared in an analogous manner to that of (±)-1-S-hexadecyl-2-O-methyl-3-O-mesylthioglycerol from 5.5 grams (0.016 mole) of (±)-1-S-hexadecyl-2-O-ethylthioglycerol and 2.2 grams (0.019 mole) of methanesulfonyl chloride. This resulted in 6.2 grams of product (94%) as an oil. $^1$H-NMR ($CDCl_3$): delta, 0.87(t, 3H, terminal methyl), 1.2–1.6[m, 31H, ($\underline{CH_2}$)$_{14}$, $\underline{CH_3}$—$CH_2$—O], 2.58(m, 2H, S—$\underline{CH_2}$), 2.62(m, 2H, CH—$\underline{CH_2}$—S), 3.08(s, 3H, $SO_2$—$\underline{CH_3}$), 3.40–3.50(m, 3H, $\underline{CH}$, $CH_3$—$\underline{CH_2}$—O), 4.35(m, 2H, $\underline{CH_2}$—$OSO_2$).

EXAMPLE 12

(±)-1-O-(1'-Naphthyl)-2-O-methyl-3-O-mesylglycerol

This compound was synthesized in an analogous manner to that of (±)-1-S-hexadecyl-2-O-methyl-3-O-mesylthioglycerol from 2.85 grams (0.012 mole) of (+)-1-O-(1'-Naphthyl)-2-O-methylglycerol and 2.1 milliliters (0.016 mole) of methanesulfonyl chloride. Purification by silica gel chromatography using a discontinuous gradient of 5:1 to 2:1 hexanes:ethyl acetate yielded 3.4 grams (89.5%) of the sulfonate ester (±)-1-O-(1'-Naphthyl)-2-O-methyl-3-O-mesylglycerol. $^1$H-NMR ($CDCl_3$): delta, 2.9(s, 3H, $SO_2CH_3$), 3.5(s, 3H, $OCH_3$), 3.8–4.0(m, 1H, $CHOCH_3$), 4.1–4.25(m, 2H, $CH_2ONaph$), 4.35–4.5(m, 2H, $\underline{CH_2}OSO_2$), 6.65–6.8(m, 1H, Naph), 7.25–7.5 (m, 4H, Naph), 7.65–7.8 (m, 1H, Naph), 8.1–8.25(m, 1H, Naph).

EXAMPLE 13

(±)-1-hexadecylthio-2-methoxy-3-bromopropane

Into a flask equipped with a magnetic stir bar, drying tube, and a reflux condenser, a solution of 3.0 grams (0.007 mole) (±)-1-S-hexadecyl-2-O-methyl-3-O-mesylthioglycerol and 2.5 grams (0.029 mole) of lithium bromide in 150 milliliters of acetone was refluxed for 24 hours with continuous stirring. The reaction was cooled to room temperature, the sodium mesylate filtered and the solvent evaporated in vacuo. The residue was dissolved in 300 milliliters of ether and extracted three times with 500 milliliter portions of sodium thiosulfate, twice with 500 milliliter portions of water, and the organic layer dried over anhydrous sodium sulfate. Filtration of the drying agent, evaporation of the ether in vacuo and subsequent silica gel chromatography (hexane:ether 9:1 as eluent) afforded 2.5 grams (87%) of an oily product. $^1$H-NMR ($CDCl_3$): delta, 0.87 (t, 3H, terminal methyl), 1.2–1.6 [m, 28H, ($\underline{CH_2}$)$_{14}$], 2.58 (m, 2H, S—$\underline{CH_2}$), 2.62 (m, 2H, CH—$\underline{CH_2}$—S), 3.38(S, 3H, O—$\underline{CH_3}$), 3.48 (m, 3H, $\underline{CH}$—$\underline{CH_2}$Br).

EXAMPLE 14

(±)-1-hexadecylthio-2-ethoxy-3-bromopropane

This compound was prepared in an analogous manner to that (±)-1-hexadecylthio-2-methoxy-3-bromopropane with 6.0 grams (0.014 mole) of (±)-1-S-hexadecyl-2-O-ethyl-3-O-mesylthioglycerol and 20.0 grams (0.07 mole) of lithium bromide. Silica gel column chromatography as before gave 5.5 grams (93%) of product as an oil. $^1$H-NMR ($CDCl_3$): delta, 0.87(t, 3H, terminal methyl), 1.2–1.6[m, 31H, ($\underline{CH_2}$)$_{14}$, $\underline{CH_3}$—$CH_2$—O], 2.58(m, 2H, S—$CH_2$), 2.62(m, 2H, CH—$\underline{CH_2}$—S), 3.3–3.5(m, 5H, $\underline{CH}$, $CH_3$—$\underline{CH_2}$—O, $\underline{CH_2}$—Br).

EXAMPLE 15

(±) -1-(1'-Naphthoxy)-2-methoxy-3-bromopropane

This intermediate was synthesized in an analogous manner to that of (±)-1-hexadecylthio-2-methoxy-3-bromothiopropane from 3.15 grams (0.010 mole) of (±)-1-O-(1'-Naphthyl)-2-O-methyl-3-O-mesylglycerol and 4.3 grams (0.041 mole) of lithium bromide in 30 milliliters of acetone, resulting in 2.7 grams (90%) of the product as an oil. $^1$H-NMR ($CDCl_3$): delta, 3.5(s, 3H, $OCH_3$), 3.6–3.9(m, 3H, $\underline{CH}$—$\underline{CH_2}$Br), 4.25 (d, 2H, $\underline{CH_2}ONaph$), 6.7–6.85 (m, 1H, Naph), 7.3–7.6(m, 4H, Naph), 7.7–7.9(m, 1H, Naph), 8.2–8.35(m, 1H, Naph).

EXAMPLE 16

(±)-3-hexadecylthio-2-methoxy-N,N-dimethyl-N-β-hydroxyethyl-1-propyl ammonium bromide Into a two neck 25 milliliter round bottom flask equipped with an air condenser, thermometer and stir bar, was placed 2.0 grams (0.005 mole) of (±)-1-hexadecylthio-2-O-methoxy-3-bromopropane, 0.5 milliliter (0.006 mole) of N,N-dimethylaminoethanol and 15 milliliters of DMF. The solution was maintained at 45°–50° Centigrade for 72 hours with continuous stirring. The reaction mixture was then cooled to room temperature, 125 milliliters of ether was added and the solution was kept at 0° Centigrade for 24 hours. The resulting precipitate (800 milligrams) was filtered and swirled with five 50 milliliter portions of ether to give (±)-3-hexadecylthio-2-methoxy-N,N-dimethyl-N-β-hydroxyethyl-1-propyl ammonium bromide (32%), (mp 107°–109° Centigrade). $^1$H-NMR ($CDCl_3$): delta, 0.87(t, 3H, terminal methyl), 1.2–1.6[m, 28H, ($\underline{CH_2}$)$_{14}$], 2.45–3.0 (m, 4H, S—$\underline{CH_2}$, $\underline{CH_2}$—S), 3.48[s, 9H, $\underline{CH_3}$—O, N($\underline{CH_3}$)$_2$], 3.9–4.3(m, 7H, $\underline{CH}$, $\underline{CH_2}N$, N—$\underline{CH_2}$—$\underline{CH_2}$—OH). Anal. ($C_{24}H_{52}NO_2SBr$) C,H,N.

EXAMPLE 17

(±)-3-hexadecylthio-2-ethoxy-N,N-dimethyl-N-β-hydroxyethyl-1-propyl ammonium bromide This product was prepared in an analogous manner to that of (±)-3-hexadecylthio-2-methoxy-N, N-dimethyl-N-β-hydroxyethyl-1-propyl ammonium bromide from 2.2 grams (0.005 mole) of (±)-1-hexadecylthio-2-ethoxy-3-bromopropane and 0.15 milliliter (0.006 mole) of N,N-dimethylaminoethanol to give 0.775 milligram (30%) of product, (mp 112°–113° Centigrade). $^1$H-NMR (CDCl$_3$): delta, 0.87(t, 3H, terminal methyl), 1.2–1.6[m, 31H, ($\underline{CH}_2$)$_{14}$, $\underline{CH}_3$—CH$_2$—O], 2.58(m, 2H, S—$\underline{CH}_2$), 2.7–2.9(m, 2H, $\underline{CH}_2$—S), 3.48[s, 6H, N($\underline{CH}_3$)$_2$], 3.9–4.3(m, 9H, $\underline{CH}$, $\underline{CH}_2$—N—$\underline{CH}_2$—$\underline{CH}_2$—OH, CH$_3$—$\underline{CH}_2$—O). Anal. (C$_{25}$H$_{54}$NO$_2$SBr) C,H,N.

EXAMPLE 18

(±)-3-hexadecylthio-2-ethoxy-N,N-dimethyl-N-gamma-hydroxypropyl-1-propyl ammonium bromide This product was prepared in an analogous manner to that of (±)-3-hexadecylthio-2-methoxy-N,N-dimethyl-N-β-hydroxyethyl-1-propyl ammonium bromide from 2.2 grams (0.005 mole) of (±)-1-hexadecylthio-2-ethoxy-3-bromopropane and 0.6 milliliter (0.006 mole) of N,N-dimethylaminopropanol to give 0.575 milligram (22%) of product, (mp 96°–98° Centigrade). $^1$H-NMR (CDCl$_3$): delta, 0.87(t, 3H, terminal methyl), 1.2–1.6[m, 31H, ($\underline{CH}_2$)$_{14}$, $\underline{CH}_3$—CH$_2$—O], 2.2(m, 2H, N—CH$_2$—$\underline{CH}_2$—CH$_2$), 2.58(m, 2H, S—$\underline{CH}_2$), 2.7–2.9(m, 2H, $\underline{CH}_2$—S), 3.48[s, 6H, N($\underline{CH}_3$)$_2$], 3.9–4.3(m, 9H, CH$_3$$\underline{CH}_2$O$\underline{CH}$, $\underline{CH}_2$—N—$\underline{CH}_2$—CH$_2$—$\underline{CH}_2$—OH). Anal. (C$_{26}$H$_{56}$NO$_2$SBr) C,H,N.

EXAMPLE 19

(±)-3-hexadecylthio-2-methoxy-N,N,N-trimethyl-1-propyl ammonium bromide

To a 100 milliliter heavy wall glass tube equipped with a magnetic stir bar, was added a solution of 2.0 grams (0.005 mole) of (±)-1-hexadecylthio-2-methoxy-3-bromopropane dissolved in 50 milliliters of CH$_3$CN and the vessel was cooled to −10° Centigrade. An excess of condensed trimethylamine was added, the tube was sealed, and the vessel was heated to 60° Centigrade for 24 hours. The reaction mixture was then cooled to room temperature, resulting in a precipitate which was filtered. The precipitate was swirled with five 50 milliliter portions of ether, the ether decanted off, and dried under vacuum, resulting in 2.1 grams (92%) of pure product, (mp 197°–199° Centigrade). $^1$H-NMR (CDCl$_3$): delta, 0.87(t, 3H, terminal methyl), 1.2–1.6[m, 28H, ($\underline{CH}_2$)$_{14}$], 2.45–3.0(m, 4H, $\underline{CH}_2$S—$\underline{CH}_2$), 3.48[s, 12H, $\underline{CH}_3$—O, N($\underline{CH}_3$)$_3$], 3.5–4.0(m, 3H, $\underline{CH}$—$\underline{CH}_2$N). Anal. (C$_{23}$H$_{50}$NOSBr) C,H,N.

EXAMPLE 20

(±)-3-(1′-Naphthoxy)-2-methoxy-N,N-dimethyl-N-β-hydroxyethyl-1-propyl ammonium bromide This analog was prepared in a manner similar to that of (±)-3-hexadecylthio-2-methoxy-N,N-dimethyl-N-β-hydroxyethyl-1-propyl ammonium bromide from 1.0 gram (0.003 mole) of (±)-1-(1′-Naphthoxy)-2-methoxy-3-bromopropane and 0.374 milliliter (0.003 mole) of N,N-dimethylaminoethanol to give 0.45 gram (35%) of the product, (decomposes>150° Centigrade). $^1$H-NMR (CDCl$_3$): delta, 3.37[d, 6H, N($\underline{CH}_3$)$_2$], 3.51(s, 3H, O$\underline{CH}_3$), 3.66–3.84(m, 3H, $\underline{CH}$OCH$_3$, $\underline{CH}_2$OH), 4.02–4.4(m, 6H, $\underline{CH}_2$NCH$_2$, C$\underline{H}_2$ONaph), 6.82(d, 1H, Naph), 7.3–7.52(m, 4H, Naph), 7.74–7.79(m, 1H, Naph), 8.14–8.2(m, 1H, Naph). Anal. (C$_{18}$H$_{26}$NO$_3$Br) C, H, N.

EXAMPLE 21

(±)-N-(2,2-Dimethyl-1,3-dioxolan-4-yl)methyl-N,N-dimethyl-β-hydroxyethyl ammonium bromide Into a 500 milliliter round bottom flask equipped with a magnetic stir bar and drying tube, a solution of 28.0 grams (0.181 mole) of 3-bromo-1,2-propanediol in 200 milliliters of acetone was added. Then, 0.5 milliliter of concentrated sulfuric acid was added and the reaction allowed to proceed at room temperature for 24 hours with continuous stirring. The reaction mixture was neutralized with 13.0 grams of K$_2$CO$_3$ for 30 minutes, the solution was filtered and the solvent evaporated in vacuo. The resulting oil was dissolved in 150 milliliter of ether, extracted three times with 150 milliliter portions of water and the organic layer dried over anhydrous sodium sulfate. The filtered ether was evaporated in vacuo and 100 milliliters of hexanes was added, resulting in two layers. The upper layer was decanted and evaporated in vacuo to provide 19.1 grams (53.5%) of (2,2-dimethyl-1,3-dioxolan-4-yl)methyl bromide. The desired analog was then prepared in an analogous manner to that of (±)-3-hexadecylthio-2-methoxy-N,N-dimethyl-N-β-hydroxyethyl-1-propyl ammonium bromide from 2.5 grams (0.013 mole) of (2,2-dimethyl-1,3-dioxolan-4-yl)methyl bromide, 1.3 grams (0.014 mole) of N,N-dimethylaminoethanol, and 15 milliliters of CH$_3$CN. Chromatography with Florisil® (CHCl$_3$:MeOH 3:1 as eluent) provided 0.860 milligrams (23%) of product as a thick oil. $^1$H-NMR (CDCl$_3$): delta, 1.25 (s, 3H, $\underline{CH}_3$), 1.35(s, 3H, $\underline{CH}_3$), 3.4–3.48[s, 6H, CH$_2$—N($\underline{CH}_3$)$_2$], 3.75–4.25(m, 9H, $\underline{CH}$, $\underline{CH}_2$—O, $\underline{CH}_2$—N—$\underline{CH}_2$—$\underline{CH}_2$—OH). Anal. (C$_{10}$H$_{22}$NO$_3$Br) C,H,N.

EXAMPLE 22

N-(2-Heptadecyl-1,3-dioxolan-4-yl)methyl-N, N-dimethyl-gamma-hydroxypropyl ammonium bromide 1,2-octadecylideneglycerol was synthesized according to Piantadosi et al., J. Org. Chem. 28, 242 (1963). The alcohol was converted in the usual manner to the bromo adduct. The final product, N-(2-Heptadecyl-1,3-dioxolan-4-yl)methyl-N,N-dimethyl-gamma-hydroxypropyl ammonium bromide, was prepared in an analogous manner to that of (±)-3-hexadecylthio-2-methoxy-N,N-dimethyl-N-β-hydroxyethyl-1-propyl ammonium bromide from 2.0 grams (0.005 mole) of (2-heptadecyl-1,3-dioxolan-4-yl)methyl bromide and 0.6 milliliter (0.006 mole) of N,N-dimethylaminopropanol in 10 milliliters of DMF (62°–65° Centigrade for 72 hours) to yield 725 milligrams (30%) of product, (mp 93°–95° Centigrade). $^1$H-NMR (CDCl$_3$): delta, 0.87(t, 3H, terminal methyl), 1.2–1.4[m, 32H, CH—($\underline{CH}_2$)$_{16}$], 2.10(m, 2H, N—CH$_2$—$\underline{CH}_2$—CH$_2$—OH), 2.60(m, 1H, OH), 3.40[s, 6H, N($\underline{CH}_3$)$_2$], 3.7–4.4 (m, 9H, $\underline{CH}_2$—N—$\underline{CH}_2$—CH$_2$—$\underline{CH}_2$—OH, $\underline{CH}$—$\underline{CH}_2$—O), 5.0 (t, 1H, O—$\underline{CH}$—O). Anal. (C$_{26}$H$_{54}$NO$_3$Br) C,H,N.

EXAMPLE 23

(±)-3-hexadecyloxy-2-methoxy-N,N-dimethyl-N-β-hydroxyethyl-1-propyl ammonium iodide and (±)-3-octadecylthio-2-methoxy-N,N-dimethyl-N-gamma-hydroxypropyl-1-propyl ammonium iodide These analogs were prepared in the usual manner according to the same procedures set forth in Examples 1, 3, 5, 7, 10, 13 and 16, (±)-3-hexadecyloxy-2-methoxy-N,N-dimethyl-N-β-hydroxyethyl-1-propyl ammonium iodide, (C$_{24}$H$_{52}$O$_3$NI) C,H,N, and (±)-3-octadecylthio-2-methoxy-N,N-dimethyl-N-gamma-hydroxypropyl-1-propyl ammonium iodide (C$_{27}$H$_{58}$O$_2$NSI) C,H,N.

EXAMPLE 24

(±)-3-1-Methyl-1-(3-hexadecyloxy-2-ethoxypropyl)-4-hydroxypiperidium iodide

Starting with (±)-1-O-hexadecyl-2-O-ethylglycerol, see Daniel, L. W. et al., *Biochem. Biophys. Res. Comm.* 151, 291 (1988), the primary hydroxyl group was mesylated as in Example 10 to give (±)-1-O-hexadecyl-2-O-ethyl-3-O-mesylglycerol. The mesylate was displaced with NaI as in Example 13 to give (±)-1-hexadecyloxy-2-ethoxy-3-iodopropane. The iodo adduct was aminated according to Example 16 with N-methyl-4-hydroxy-piperidine to give 1-methyl-1-(3-hexadecyloxy-2-ethoxypropyl)-4-hydroxypiperidium iodide.

EXAMPLE 25

Preparation of Protein Kinase C (PKC)

PKC was prepared and assayed as described previously. See Daniel, L. W. et al., *Biochem. Biophys. Res. Comm.* 151, 291 (1988). In brief, HL-60 cells were grown in 75 milliliter flasks, harvested and washed with ice-cold normal saline. After centrifugation (600×g, 5 minutes, 4° Centigrade), the cell pellet was resuspended (20 mM Tris-HCl, pH 7.5, 2 mM EDTA, 10 mM EGTA, 50 mM 2-mercaptoethanol, 2 mM phenylmethylsulfonyl fluoride) and sonicated for 20 s with a stepped microprobe sonciator. Unbroken cells were removed by centrifugation as above and the supernatant centrifuged (65,000×g, 90 minutes, 4° Centigrade). The supernatant from this step (cytosol) was then fractionated on a 1×8 cm DEAE-Sephacel column after addition to sucrose to a final concentration of 10%. After equilibrating the column (20 mM Tris, pH 7.5, 0.2 mM EDTA, 0.2 mM EGTA, 50 mM 2-mercaptoethanol, 10% sucrose), the sample was loaded and unbound material was washed through with 40 milliliters of the equilibrating buffer. The PKC was eluted by a gradient from 0–0.5M NaCl in the buffer described above. Fractions of 1 milliliter were collected at 25 milliliters per hour and 0.05 milliliter aliquots assayed for PKC activity as described below. The fractions with the highest activity were pooled and used in further experiments.

EXAMPLE 26

Assay of Protein Kinase C Activity

The assays were done at pH 7.5 in a total volume of 0.25 milliliter and all tubes contained 25 mM Tris, 10 mM MgCl$_2$, 40 µg per milliliter histone, 10 µM ATP (including 1 µCi of [gamma-$^{32}$P]-ATP), 0.1 mM CaCl$_2$, 20 µg per milliliter phosphatidylserine, 0.05 milliliter of the PKC preparation and 2.5 µM of oleoylacetylglycerol (OAG). Enzymatic activity was determined as the incorporation of $^{32}$P from [gamma-$^{32}$P]-ATP into histone in the presence of Ca$^{2+}$, phosphatidylserine, and OAG. Reactions were initiated by the addition of the enzyme preparation and halted after 20 minutes at 30° Centigrade by the addition of 0.05 milliliters of bovine serum albumin (10 milligrams per milliliter) and 1 milliliter 25% ice-cold trichloroacetic acid. The tubes were kept on ice and then filtered in a millipore vacuum box using Millipore® HA filters and washed with 25% trichloroacetic acid. The radioactivity bound to the filters was determined by scintillation spectrometry in 5 milliliters Budget Solve®. The amount of enzyme used was shown to result in linear activity for at least 20 minutes and the assay was linearly dependent on the amount of enzyme used. The analog to be tested was dissolved in ethanol, and added directly into the reaction mixture before the addition of PKC. As a control, 0.1% ethanol was included in the samples with the enzyme but with no inhibitor.

Assay of the following compounds in accordance with the foregoing procedures gave the data reported in Table 1 below:

(A) (±)-3-hexadecylthio-2-methoxy-N,N-dimethyl-N-β-hydroxyethyl-1-propyl ammonium bromide;

(B) (±)-3-hexadecylthio-2-ethoxy-N,N-dimethyl-N-β-hydroxyethyl-1-propyl ammonium bromide;

(C) (±)-3-hexadecylthio-2-ethoxy-N,N-dimethyl-N-gamma-hydroxypropyl-1-propyl ammonium bromide;

(D) (±)-3-hexadecylthio-2-methoxy-N,N,N-trimethyl-1-propyl ammonium bromide;

(E) (±)-3-(1'-Naphthoxy)-2-methoxy-N,N-dimethyl-N-β-hydroxyethyl -1-propyl ammonium bromide;

(F) (±)-N-(2,2-Dimethyl-1,3-dioxolan-4-yl)methyl-N,N-dimethyl-β-hydroxyethyl ammonium bromide;

(G) (±)-N-(2-heptadecyl-1,3-dioxolan-4-yl)methyl-N,N-dimethyl-gamma-hydroxypropyl ammonium bromide;

(H) (±)-3-hexadecyloxy-2-methoxy-N,N-dimethyl-N-β-hydroxyethyl-1-propyl ammonium iodide; and (I) (±)-3-octadecylthio-2-methoxy-N,N-dimethyl-N-gamma-hydroxypropyl-1-propyl ammonium iodide.

TABLE 1

| | Percent Protein Kinase C[1] Activity Retained Following Incubation with Quaternary Ammonium Alkylglycerols[2] | | | | | | |
|---|---|---|---|---|---|---|---|
| Compound | 0.0 | 1.25 | 2.5 | 5.0 | 10.0 | 20.0 | 40.0 µM |
| A | 100 | 97 ± 14 | 90 ± 13 | 73 ± 12 | 60 ± 4 | 54 ± 11 | 42 ± 10 |
| B | 100 | 92 ± 5 | 84 ± 7 | 70 ± 7 | 70 ± 16 | 66 ± 25 | 47 ± 12 |
| C | 100 | 78 ± 9 | 64 ± 12 | 67 ± 18 | 60 ± 19 | 59 ± 15 | 37 ± 6 |
| D | 100 | 112 ± 23 | 88 ± 5 | 81 ± 7 | 74 ± 4 | 54 ± 9 | 29 ± 5 |
| E | 100 | 99 ± 3 | 99 ± 5 | 83 ± 20 | 89 ± 13 | 87 ± 12 | 90 ± 6 |
| F | 100 | 88 ± 1 | 84 ± 1 | 87 ± 3 | 88 ± 6 | 96 ± 14 | 87 ± 8 |
| G | 100 | 44 ± 17 | 43 ± 3 | 26 ± 8 | 12 ± 3 | 9 ± 3 | 9 ± 2 |
| H | 100 | 107 ± 20 | 95 ± 20 | 87 ± 18 | 64 ± 19 | 42 ± 15 | 29 ± 9 |
| I | 100 | 75 ± 13 | 56 ± 11 | 49 ± 23 | 39 ± 21 | 27 ± 14 | 23 ± 8 |

[1]PKC was isolated from HL-60 cells as described in Example 25.
[2]Each analog was losted in duplicate in three separate trials.

EXAMPLE 27

HL60 Cell Growth Inhibition by Quaternary Amine-Containing Ether Lipid Derivatives A number of the compounds disclosed herein have been tested against the HL60 human leukemia cell line to assess their cytotoxic potential. These analogs were investigated in parallel with ET-18-OMe which was used as the reference compound. The methodologies used in this investigation were the same as described in A. Noseda, M. Berens, C. Piantadosi, and E. J. Modest, *Lipids* 22, 878–883, 1987. In brief, HL60 cells at a concentration of 5×105 were incubated in wells with one milliliter medium with the experimental drug in parallel with the same concentration of cells with ET-18-OMe (standard) or EtOH (control). After 48 hours of incubation the cells were counted using the trypan blue dye exclusion technique to determine the effect of the drug on cell growth. The experimental drug and ET-18-OMe were tested at the same concentrations, e.g., 10, 5, 2.5 and 1.25 µM.

Results are shown in Table 2 below. These results show cytotoxic activity against HL60.

ET-18-OMe shows an activity that is consistent with previous reports against the cell line tested (see Noseda et al., *Lipids* 22, 878–883, (1987).

TABLE 2

|  | $ID_{50}$ | $ID_{50}$; ET-18-OMe |
| --- | --- | --- |
| 1-(3-hexadecyloxypropyl) pyridium bromide (KLM 70) | 0.8 | 1.7 |
| 3-hexadecyloxy-N,N,N-trimethyl-1-propyl ammonium bromide (KLM 69) | 1.6 | 1.9 |
| (±)-3-octadecylthio-2-methoxy-N,N-dimethyl-N-gamma-hydroxy propyl-1-propyl ammonium bromide (CJM 44) | 3.4 | 2.3 |
| (±)-3-hexadecylthio-2-methoxy-N,N-dimethyl-N-β-hydroxyethyl-1-propyl ammonium bromide (CJM 57) | 4.6 | 2.3 |
| (±)-N-(2-heptadecyl-1,3-dioxolan-4-yl)methyl-N,N-dimethyl-gamma-hydroxypropyl ammonium bromide (CJM 60) | 6.5 | 2.2 |
| ET-18-OMe | 2.5 | — |
| (±)-1-methyl-1-(3-hexadecyloxy-2-ethoxypropyl)-4-hydroxy piperidinium iodide (CJM PIPER) | 2.8 | 1.9 |

EXAMPLES 28–41

Preparation of:

(I) 2-hexadecanoyloxy-N,N-dimethyl-N-β-hydroxyethyl-1-ethyl ammonium iodide.

(II) 2-octadecanoyloxy-N,N-dimethyl-N-β-hydroxyethyl-1-ethyl ammonium iodide.

(III) 2-dodecyloxy-N,N-dimethyl-N-β-hydroxyethyl-1-ethyl ammonium iodide.

(IV) 2-tetradecyloxy-N,N-dimethyl-N-β-hydroxyethyl-1-ethyl ammonium iodide.

(V) 2-hexadecyloxy-N,N-dimethyl-N-β-hydroxyethyl-1-ethyl ammonium iodide.

(VI) 2-hexadecyloxy-N,N-dimethyl-N-gamma-hydroxypropyl-1-ethyl ammonium iodide.

(VII) 2-hexadecyloxy-N,N-dimethyl-N-delta-hydroxybutyl-1-ethyl ammonium iodide.

(VIII) 2-octadecyloxy-N,N-dimethyl-N-β-hydroxyethyl-1-ethyl ammonium iodide.

(IX) 2-Phenoxy-N,N-dimethyl-N-β-hydroxyethyl-1-ethyl ammonium iodide.

(X) (±)-3-octadecyloxy-2-hydroxy-N,N-dimethyl-N-β-hydroxyethyl-1-propyl ammonium iodide.

(XI) (±)-3-hexadecyloxy-2-acetoxy-N,N-dimethyl-N-β-hydroxyethyl-1-propyl ammonium iodide.

(XII) (±)-3-hexadecyloxy-2-methoxy-N,N-dimethyl-N-β-hydroxyethyl-1-propyl ammonium iodide.

(XIII) 3-octadecyloxy-N,N-dimethyl-N-β-hydroxyethyl-1-propyl ammonium iodide.

The following general methods were employed. Melting points were determined on a Thomas Hoover capillary melting point apparatus and are uncorrected. Nuclear magnetic resonance (NMR) spectra were recorded on a Jeol-JNM-Fx60 spectrometer, and chemical shifts in parts per million (ppm) were reported relative to the internal reference, tetramethylsilane (TMS). Deuterochloroform was used as the NMR solvent unless otherwise specified. Infrared spectra (IR) were recorded on a Perkin-Elmer 1320 spectrophotometer. Micro thin layer chromatography (mTLC) was performed on 1×3 inch 200µ, Whatman TLC precoated silica gel MK6F plates. Compounds were visualized by iodine and short wave UV light. UV bands were detected on a Chromato-Vue, model CC-20. Column chromatography was performed on 70–230 mesh(ASTM) silica gel from EM Science. Dimethylformamide (DMF) was purified by shaking with solid potassium hydroxide and then lime, followed by distillation at atmospheric pressure. Tetrahydrofuran (THF) was dried over molecular sieves. Elemental analysis for carbon, hydrogen, and nitrogen were performed by Atlantic Microlabs, Inc. (Atlanta, Ga.).

The synthesis of 2-Hexadecyloxy-N,N-dimethyl-N-gamma-hydroxypropyl-1-ethyl ammonium iodide illustrates the basic procedures used for the preparation of these lipid analogs. Others are synthesized essentially by the same procedure utilizing the appropriate intermediates.

(a) Preparation of ethylene glycol monobenzyl ether. This compound was synthesized according to the procedure of Butler et al., *J. Am. Chem. Soc.* 60, 1472 (1938).

(b) 1-Hexadecyloxy-2-benzyloxyethane. To a three necked round bottom flask equipped with a stir bar, dropping funnel reflux condenser and a gas inlet adapter, was added 20 milliliters of dry THF and the flask cooled to 0°–5° Centigrade in an ice bath. To the stirring solvent, sodium hydride, 3.41 grams (71 millimoles) of a 50% oil dispersion, was added with 15 milliliters of dry THF under an atmosphere of nitrogen. After a slurry was formed, 11 grams (72 millimoles) of ethylene glycol monobenzyl ether in 75 milliliters of dry THF was added dropwise. Stirring was continued for two hours until the evolution of hydrogen ceased. To this, 21.7 grams (71 millimoles) bromohexadecane was added and the mixture was refluxed overnight. Ice water was added cautiously to the cooled reaction mixture to quench any unreacted sodium hydride. The mixture was extracted with 300 milliliter of ether. The ether solution was washed with 4×100 milliliter portions of water and dried over anhydrous magnesium sulfate. The solvent was removed in vacuo. The crude product was chromatographed on silica gel and eluted with hexane, hexane/ether 9:1, 8:2 to give 5.75 grams of a pure oil, yield 21.5%, mTLC hexane/ether 9:1.

(c) 2-Hexadecyloxyethanol. A solution of 6.9 grams (18.3 millimoles) 1-hexadecyloxy-2-benzyloxyethane with 0.6 gram of 10% Pd/C in 100 milliliters of hexane was hydrogenated for four hours at 30 psi. The catalyst was removed by gravity filtration and the hexane was evaporated in vacuo to give 4.5 grams of an oil. The oil was dissolved in hexane and left at 15° Centigrade. The crystalline product was suction filtered to give 3.3 grams, yield 63%, M.P. 41°–42° Centigrade, mTLC hexane/ether 9:1.

(d) 1-Hexadecyloxy-2-mesyloxyethane. 1-Hexadecyloxy-2-ethanol, 9.9 grams (34 millimoles) was converted to its mesylate derivative in the presence of triethylamine according to the procedure of Crossland et al., *J. Org. Chem.* 25, 3195 (1970). The resultant oil was dissolved in hexane and kept at 15° Centigrade. The crystalline product was suction filtered to give 8.8 grams, yield 70%, M.P. 44°–45° Centigrade, mTLC chloroform/ether 4:1.

(e) 1-Hexadecyloxy-2-iodoethane. The iodo derivative was obtained by refluxing 8.8 grams (24 millimoles) of 1-hexadecyloxy-2-mesyloxyethane and 10.8 grams (72 millimoles) of NaI in dry acetone for 24 hours by the procedure of Gibson et al., *J. Am. Chem. Soc.* 91, 4771 (1969). The crude oily residue was chromatographed on silica gel and eluted with hexane, hexane/ether, 9.5:0.5, to give 6.1 grams of pure semisolid product, yield 64%, mTLC hexane/ether 9.5:0.5.

(f) 2-Hexadecyloxy-N,N-dimethyl-N-gamma-hydroxypropyl-1-ethyl ammonium iodide. To a two necked round bottom flask equipped with a stir bar, thermometer, air condenser and drying tube (Drierite), was added 2 grams (5 millimoles) of 1-hexadecyloxy-2-iodoethane, 0.57 gram (5.5 millimoles) N,N-dimethylaminopropanol and 40 milliliters of DMF. The solution was heated and maintained at 48°–50° Centigrade for three days with stirring. See A. Rosenthal and P. Geye, *J. Biol. Chem.* 225, 2202 (1960). After cooling to room temperature, anhydrous ether was added to the reaction mixture which was kept at 15° Centigrade. The crystalline product was suction filtered and recrystallized from DMF and ether. The pure crystalline material weighed 0.84 gram, yield 34%, M.P. 73°–75° Centigrade, mTLC chloroform/methanol 9:1. Anal. ($C_{23}H_{50}NO_2I$) C,H,N.

EXAMPLES 42–43

Cytostatic Activity of Lipid Analogs on KB and 77 Cells and Other Cell Lines All cells were grown in Eagle's minimum essential medium supplemented with 10% fetal bovine serum with the exception of HL-60 and K562-4 cells which were grown in RPMI 1640 medium supplemented with 10% fetal bovine serum. The KB and $MH_1C_1$ cells, from a human nasopharyngeal carcinoma and rat hepatoma, respectively, were from American Type Culture Collection. The ChaGo cells, a human lung carcinoma, was generously provided by Dr. A. H. Tashjian. The human promyeloblastic leukemia cells, K562-4 were kindly supplied by Dr. Bismarck Lozzio. HL-60 cells, a human promyelocytic leukemia, and P388 cells, a mouse leukemia, were obtained from Dr. Y.-C. Cheng. The 77 cells were put into culture by us by excising the 7777, Morris hepatoma from a rat graciously supplied by the late Dr. H. P. Morris.

Cells were transferred or removed from monolayers for counting after a one or two minute incubation with 0.02% sodium ethylenediamine tetraacetate in phosphate-buffered saline to dislodge the cells. Flasks were seeded at a density of $1\times10^3$ cells per $cm^2$ or $2\times10^4$ per milliliter for suspension cultures. The HL-60 and K562-4 suspension cultures were used about 24 hours after seeding. The compounds to be tested were diluted to various concentrations and added to the monolayer cultures. All of the test compounds were dissolved in 10% dimethyl sulfoxide (DMSO) at concentrations that would give a final DMSO concentration of 0.1%. Control flasks contained 0.1% DMSO. Control cell replication was followed until approximately three doublings had occurred, and then all of the treated cells were counted. The compound concentrations for 50% inhibition of replication ($IC_{50}$) were determined graphically from these results.

For the KB cells which grow as monolayers, the cells were removed from the flasks as described above and counted. A suitable dilution was made of the cells so that 50–200 colony-forming cells were added to fresh medium in flasks and incubated for 12 days. The medium was drained and the colonies fixed and stained with 0.5% methylene blue in 50% ethanol. Colonies of about 50 or more cells were counted and the plating efficiency calculated as the percent cells that were able to form colonies.

For the K562-4 cells grown in suspension, the dilute agar method as described by Chu and Fischer, *Biochem. Pharmacol.* 17 753 (1968), was used.

The primary screen employed for cytotoxicity measurement was inhibition of KB and 77 cell multiplication. The KB cells represented cells with low alkyl cleavage activity (less than the detectable level of 0.1–0.2 units per milligram protein by our assay procedure) and the 77 cells represented cells similar to normal cells with relatively high alkyl cleavage activity (1.6 units per milligram of protein). Our value for the cleavage activity of cultured 77 cells agrees well with the value of 1.4 units per milligram of protein reported by Soodsma et al, *Cancer Res.* 30, 309 (1970), for freshly excised 7777 Morris hepatoma tissue. In further confirmation of our assay procedure, we obtained a value of 12.6±4.1 units per milligram of protein in excised rat liver compared to 7.3 units per milligram of protein in rat liver measured by Soodsma et al.

$IC_{50}$ values for the compounds of Examples 28–41 are given in Table 3 below.

TABLE 3

| $IC_{50}^a$ (µM) Values of Lipid Analogs for KB and 77 Cells | | | |
|---|---|---|---|
| Analog | KB | 77 | 77/KB$^d$ |
| I | 50,100 | c | |
| II | 16 | c | |
| III | 0.78 ± 0.03 | 4.73 ± 0.87 | 6.1 ± 1.15 |
| IV | 0.32 ± 0.12 | 1.53 ± 0.23 | 4.8 ± 1.94 |
| V | 0.33 ± 0.12 | 1.42 ± 0.50 | 4.3 ± 2.15 |
| VI | 0.23 ± 0.07 | 2.05 ± 0.91 | 8.9 ± 4.79 |
| VII | 0.44 ± 0.11 | 2.27 ± 0.93 | 5.2 ± 2.50 |
| VIII | 0.30 ± 0.14 | 1.80 ± 0.81 | 5.8 ± 3.8 |
| IX | b | c | |
| X | 0.35 ± 0.05 | 1.33 ± 0.40 | 2.9 ± 0.96 |
| XI | 0.43 ± 0.05 | 1.35 ± 0.64 | 3.1 ± 1.51 |
| XII | 0.26 ± 0.05 | 1.27 ± 0.41 | 4.9 ± 1.84 |
| XIII | 0.70 ± 0.08 | 2.50 ± 0.90 | 4.3 ± 1.60 |

$^a$Inhibitory concentration 50 ($IC_{50}$) is the concentration which inhibits the replication of test cell by 50% after the untreated or control cells have doubled three times. Most values represent averages of three of four determinations ± one standard deviation.
$^b$No inhibition up to 100 µM.
$^c$Not determined.
$^d$Ratio ± Standard Error of the Quotient of two means.

It is of interest to note here that similar to the cytotoxic synergism of ET-18-OCH$_3$ and vincristine reported by Andreesen et al., *Blood* 54, 519 (1979), against human leukemic cells, VIII acted synergistically with vincristine against KB cells. For example, 1 µM VIII reduced cell number to 45% of control and 0.004 µg per milliliter vincristine caused a reduction to 27% of control. Thus, the two agents together should have reduced cell number to 12% of control if they acted additively. Instead, when the two compounds were added together at these concentrations cell number was reduced to 2% of control, a synergistic effect.

A few of the analogs were tested against other cultured cancer cell lines (Table 4). Three other lines of human origin were used, ChaGo, K562-4, and HL-60. Both the ChaGo and K562-4 lines were inhibited by the analogs tested but the $IC_{50}$ values approximated those obtained against the 77 cells. ChaGo cells partly were chosen because of their slow growth or long doubling time (about 45 hours in our hands). The HL-60 inhibition by VI was similar to that obtained for KB cells. The P388 mouse leukemia line (doubling time 17 hours) was tested only with VIII mainly as a preliminary to in vivo testing. In the one test, the $IC_{50}$ of 0.42 µM was comparable to the 0.30 µM $IC_{50}$ for KB cells. Perhaps the most intriguing result was obtained with $MH_1C_1$ cells. These are a line of rat hepatoma cells derived from Morris hepatoma 7795. There are very slow growing (doubling time about 180 hours) cells. These cells, for the two analogs tested, VIII and XIII are two to three times less sensitive to growth inhibition than 77 cells.

TABLE 4

$IC_{50}$ Values of Lipid Analogs for Other Cell Lanes

| Cell Line | Compound | $IC_{50}$ (µM) |
|---|---|---|
| ChaGo | VIII | 1.0 |
| | X | 1.7, 2.8 |
| | XI | 1.2 |
| X562-4 | VI | 2.2 ± 0.41 |
| | VIII | 1.9 |
| | X | 2.5 |
| | XI | 3.5 |
| | XIII | 1.4 |
| P388 | VIII | 0.42 |
| $MH_1C_1$ | VIII | 6.4, 7.7 |
| | XIII | 2.9 |
| HL-60 | VI | 0.45 ± 0.011 |

EXAMPLE 44

In vivo anti-tumor activity

P388 mouse leukemia cells were transplanted by intraperitoneal injection of 1×106 cells into $BDF_1$ female mice on day 0. Treatments were begun on day 1. Control mice received the vehicle for the test compounds.

Compound VI appeared to have in vivo activity against P388. Treatment on days 1, 5, and 9 with 50 and 75 milligrams per kilogram, increased survival by 26% and 48%, respectively. One 50 milligrams per kilogram dose on day 1 did not affect survival time but 75 milligrams per kilogram on days 1 and 2 reduced survival by 48% and a single 100 milligram per kilogram dose on day 1 killed all the mice by day 2.

EXAMPLES 45–46

Effects of Ether Phospholipid Analogs on Viral Plaque Formation

The inhibitory effects of ether phospholipid analogs on the replication of human immunodeficiency virus type 1 (HIV-1) virus in cells was examined by the plaque assay procedure of P. Nara et al., *Aids Research and Human Retroviruses* 3, 283 (1987). This procedure was modified by eliminating the inclusion of DEAE-Dextran which we found toxic to CEM-SS cell growth if used to enhance attachment of the cells to the plastic wells. Dextran sulfate was used as a positive control. In brief, CEM-SS cell monolayers were pretreated with inhibitor for 30 minutes at 37° Centigrade, before infection with HIV-1. Infected cells were overlaid with RPMI-1640 plus 10% FBS supplemented with different concentrations of inhibitor. Plaques were counted at five days after infection. Results are reported in Table 5 below. The name for Inhibitor CJM 57 is given in Table 2 above.

TABLE 5

Effect of Dextran Sulfate and CJM57 on HIV-1 Plaque Formation

| Inhibitor | Concentration (µM) | Plaque Count | Inhibition (%) |
|---|---|---|---|
| Control | 0 | 15,8 | 0 |
| Dextran Sulfate | 10 | 2,0 | 91 |
| | 2 | 0,0 | 100 |
| | 1 | 0,2 | 91 |
| CJM57 | 2 | 0,2 | 91 |
| | 0.4 | 3,1 | 83 |
| | 0.2 | 8,5 | 43 |

The procedure described above was repeated with both CJM57 and ET-18-OMe. The results of this repetition are shown in Table 6 below. These results show antiviral activity for both CJM57 and ET-18-OMe.

TABLE 6

Effect of CJM57 and ET-18-OMe on HIV-1 Plaque Formation

| Inhibitor | Conc (µM) | Plaque Count | Inhibition (%) |
|---|---|---|---|
| Inhibitors Added 30 Minutes Before HIV-1 Infection | | | |
| Control | 0 | 58,65,122,68 | 0 |
| CJM57 | 2.0 | 11,12 | 85 |
| | 0.4 | 35,29 | 38 |
| | 0.2 | 77,30 | 30 |
| ET-18-OMe | 2.0 | 60,23 | 45 |
| | 0.4 | 47,92 | 9 |
| | 0.2 | 137,120 | 0 |
| Inhibitors Added 60 Minutes After HIV-1 Infection | | | |
| Control | 0 | 68,65,87 | 0 |
| CJM57 | 2.0 | 2,2 | 97 |
| | 0.4 | 21,42 | 59 |
| | 0.2 | 31,78 | 28 |
| ET-18-OMe | 2.0 | 27,44 | 64 |
| | 0.4 | 75,85 | 0 |
| | 0.2 | 84,65 | 0 |

EXAMPLES 47–48

The investigations reported in Examples 45–46 above were extended with the following compounds:

(A) (±)-1-O-octadecyl-2-O-methylglycero-3-phosphocholine (Et-18-OMe);

(B) (±)-1-S-hexadecyl-2-O-ethylthioglycero-3-phosphocholine;

(C) (±)-1-N-(octadecanoyl)-2-O-ethylaminoglycero-3-phosphocholine;

(D) (±)-1-O-hexadecyl-2-O-ethylglycero-3-phosphoric acid-2'-N-isopropyl-ammonium ethyl ester;

(E) (±)-3-hexadecylthio-2-methoxy-N,N-dimethyl-N-β-hydroxyethyl-1-propyl ammonium bromide;

(F) (±)-3-hexadecylthio-2-ethoxy-N,N-dimethyl-N-β-hydroxyethyl-1-propyl ammonium bromide;

(G) (±)-3-octadecylthio-2-methoxy-N,N-dimethyl-N-gamma-hydroxypropyl-1-propyl ammonium iodide;

(H) (±)-N-(2-heptadecyl-1,3-dithiolan-4-yl)methyl-N,N-dimethyl-gamma-hydroxypropyl ammonium bromide;

(I) (±)-1-methyl-1-[3-hexadecyloxy-2-ethoxypropyl]-4-hydroxypiperidium iodide; and (J) 2-hexadecyloxymethyl-decane-1,2-diol.

By way of further background, in our assay HIV-1 syncytial plaques are seen as large, multicellular foci (10 to 25 nuclei/syncytium) that appear either brown and granular or clear. Since the number of HIV-1 syncytial plaques correlates with reverse transcriptase (RT) and p24 core antigen activity in the HIV-1 infected cell overlay fluids, the syncytial plaque assay can be used to quantify the amount of infectious virus. Reverse transcriptase activity was assayed according to a described procedure (B. J. Poeisz et al., *Proc. Natl. Acad. Sci. (U.S.A.)* 0.77, 7415 (1980)). The activity of p24 core antigen induced by HIV-1 infection of CEM-SS cells was measured spectrophotometrically using the commercial Abbott EIA.

Our initial assay for potential antiviral activity of EL analogs involves treating CEM-SS cell monolayers with varying concentrations of Compound E above starting thirty minutes before HIV-1 infection. For a positive reference dextran sulfate was used, a known inhibitor of HIV-1 binding to target T-cells, H. Mitsuya et al., *Science* 240, 646 (1988). Results indicate that 1 and 10 µM dextran sulfate inhibited HIV-1 plaque count by 92 and 100%, respectively, compared to untreated virus infected control cells. Compound E inhibited HIV-1 plaque count 43%, 83%, and 91% at concentrations of 0.2, 0.4, and 2.0 µM, respectively, compared to untreated controls. These data indicate that when Compound E is added before virus infection it inhibits HIV-1 plaque formation in a concentration-dependent manner. In other experiments addition of 0.2, 0.4 and 2.0 µM Compound E starting sixty minutes after HIV-1 infection inhibited HIV-1 plaque formation 28%, 59% and 97% respectively, compared to untreated controls. In summary, Compound E has anti-HIV-1 activity if added to cells before or after HIV-1 infection.

Since ether lipid (EL) analogs are membrane interactive, see, e.g., A. Noseda et al., *Biochim. Biophys. Acta* 945, 92 (1988), we determined whether Compound E could directly inactivate extracellular HIV-1 infectivity. About 350 plaque forming units of HIV-1 were mixed with antiviral concentrations (2.0 µM) of E or with control medium alone in a total volume of 100 µl. After three hours of incubation at 37° C., the virus compound and virus medium mixtures were diluted 20-fold to reduce the concentration of Compound E below a significant antiviral concentration. Aliquots (100 µl) of the diluted HIV-1 were added to CEM-SS cell monolayers to measure residual virus infectivity by plaque count. A mean of 22 plaques (N=2) were counted for Compound E-treated HIV-1 and a mean of 27 plaques (N=2) for medium-treated HIV-1. These data indicate that E does not inactivate extracellular HIV-1 infectivity. In similar experiments Compound E (2 µM) neither inhibits herpes simplex virus type 2 (HSV-2) plaque formation in Vero cell monolayers nor directly inactivates extracellular HSV-2 infectivity. Collectively, these data indicate that Compound E has selective inhibitory activity against HIV-1 plaque formation.

Next investigated were the correlations of EL analog structure with anti-HIV-1 and anti-cell growth. The experimental method used six serial two-fold dilutions of EL that spanned concentrations above and below a concentration that inhibits HIV-1 plaque count, cell growth ($^3$H-TdR uptake into cell DNA) or in vitro PKC activity by 50% (inhibitory concentration$_{50}$=IC$_{50}$) compared to an appropriate mock treated control. Table 7 summarizes data on IC$_{50}$ of phosphorus and non-phosphorus compounds for HIV-1 plaque formation and cell growth. Among the phosphorus EL, potent anti-HIV activity was observed with Compounds A, B and C. The anti-HIV concentrations for Compounds B (IC$_{50}$32 0.6 µM) and C (IC$_{50}$=0.2 µM) were at least sevenfold and thirty-fold, respectively, below the IC$_{50}$ for cell growth (IC$_{50}$=4.2 and 6.6 µM, respectively). In contrast, Compound D has no demonstrable activity against HIV-1 plaque formation (Table 7).

TABLE 7

Effect of Type A Phosphorus and Type B Non-Phosphorus EL Analogs on HIV-1 Plaque Formation and Cell Growth[1]

| | Inhibitory Concentration$_{50}$ (µM) For: | |
|---|---|---|
| | HIV-1 Plaque Formation | CEM-SS Cell Growth |
| Phosphorus Ether Lipids | | |
| A | 1.4 ± 0.45 | 4.4 |
| B | 0.6 ± 0.28 | 4.2 |
| C | 0.2 ± 0.02 | 6.6 |
| D | >6.0 | 7.0 |
| Nonphosphorus Ether Lipids | | |
| E | 0.37 ± 0.01 | 3.2 |
| F | 0.63 ± 0.18 | 5.4 |
| G | 0.52 ± 0.33 | 3.4 |
| H | 0.39 ± 0.02 | 3.0 |
| I | 0.33 ± 0.01 | 1.6 |
| J | >10.0 | >20.0 |

[1]Serial 2-fold dilutions of compounds are used. HIV-1 plaque formation is measured in CEM-SS cell monolayers by having compound present starting sixty minutes after virus infection. IC$_{50}$ values for HIV-1 plaque formation are x ± one SD., N = 4. CEM-SS cell growth is measured in suspension cultures by treating the cells with compound for 48 hours at 37° C. and then adding 1 µCi of $^3$H-TdR (S.A. = 20 Ci/mmole) for 8 hours at 37° C. to measure DNA synthesis. IC$_{50}$ values for CEM-SS growth are x of a representative experiment, N = 3.

Also, the natural phospholipid found in surfactant dipalmitoyl-phosphatidylcholine has an IC$_{50}$ for HIV-1 plaque formation and CEM-SS cell growth greater than 1362 µM and 681 µM, respectively. Five nonphosphorus ether lipid analogs (Compounds E, F, G, H, and I) have significant anti-HIV-1 activity (IC$_{50}$=0.37, 0.63, 0.52, 0.39 and 0.33, µM, respectively) whereas Compound J did not inhibit HIV-1 plaque formation (Table 7). The IC$_{50}$ of these analogs active against HIV-1 plaque formation are four-fold to eight-fold below the IC$_{50}$ for cell growth.

EXAMPLE 49

This example demonstrates the effect of ether lipid E from Examples 47–48 and ET-18-OMe on HIV-1 infectious virus multiplication as measured by syncytium plaque assay and reverse transcriptase activity. In brief, CEM-SS cells were infected with HIV-1. At various times after infection (3, 6, 8, 10, 13 days) the overlay fluids were replaced with fresh medium. Overlay fluids replaced on days 8, 10 and 13 were saved at −80° C. to measure HIV-1 plaque forming units according to our described protocol above and RT activity (described by Poiesz et al., *Proc. Natl. Acad. Sci. U.S.A.* 77, 7415 (1980)). Results are given in Table 8 below.

TABLE 8

Effect of Ether Lipids on Infectious HIV-1
Multiplication and Reverse Transcriptase Activity

| Compounds | Conc (μM) | (Plaque Forming Units/ ML × 10⁻²) % of Control at Days After Infection | | | (RT Activity/ML × 10⁻⁶) | | |
|---|---|---|---|---|---|---|---|
| | | 8 | 10 | 13 | 8 | 10 | 13 |
| Control | 0 | 100(2) | 100(45) | 100(85) | 100(18.4) | 100(78.4) | 100(84.4) |
| ET-18-OMe | 0.2 | 395 | 287 | 89 | 54 | 192 | 94 |
| | 0.4 | 25 | 30 | 35 | 15 | 90 | 161 |
| | 2.0 | 0 | 33 | 30 | 6 | 6 | 174 |
| E | 0.2 | 100 | 143 | 100 | 33 | 85 | 133 |
| | 0.4 | 75 | 23 | 47 | 10 | 43 | 155 |
| | 2.0 | 0 | 49 | 18 | 18 | 30 | 102 |

These results indicate that both Compound E and ET-18-OMe markedly inhibit infectious virus production and reverse transcriptase activity in a dose-dependent manner measured between 8 and 10 days after HIV-1 infection. At 13 days, reverse transcriptase activity increases whereas infectious virus production is still inhibited in cells treated with Compound E and ET-18-OMe. These data are interpreted to suggest that at 13 days after infection and treatment the cells are lysed by virus infection releasing reverse transcriptase into the culture medium. However, virus produced in the compound treated cells is defective in infectivity measured by syncytium plaque assay.

The foregoing examples are illustrative of the present invention, and are not to be taken as restrictive thereof. Among other things, those skilled in the art will appreciate minor additions and alterations which can be made to the compounds disclosed above without departing from the concept which is the present invention. Accordingly, the applicants' invention is to be defined by the following claims, with equivalents of the claims to be included therein.

That which is claimed is:

1. A compound of the formula:

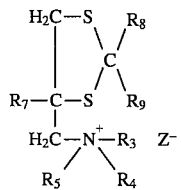

wherein:

$R_7$ is hydrogen, phenyl, or linear or branched, saturated or unsaturated C1–C16 alkyl containing not more than four double bonds or one triple bond;

$R_2$ is hydrogen or saturated or unsaturated, linear or branched C1–C5 alkyl;

$R_9$ is saturated or unsaturated, linear or branched C1–C19 alkyl containing not more than four double bonds;

$R_3$ is linear or branched, saturated or unsaturated C1–C20 alkyl containing not more than four double bonds, is hydroxy substituted at the terminal carbon and is substituted with zero to three additional hydroxy groups;

$R_4$ is C1–C5 alkyl;

$R_5$ is C1–C5 alkyl; and $Z^-$ is a pharmaceutically acceptable anion.

2. A compound according to claim 1, wherein $R_3$ is linear or branched, saturated or unsaturated C1–C18 alkyl containing not more than three double bonds, and which is substituted with one to three hydroxy groups; wherein $R_4$ is methyl, ethyl, or propyl; and wherein $R_5$ is methyl, ethyl, or propyl.

3. A pharmaceutical composition comprising a pharmaceutical carrier in combination with an amount of a compound of the formula:

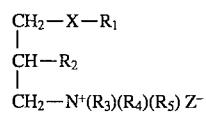

wherein:

X is S or NHC(O);

$R_1$ is linear or branched, saturated or unsaturated C14–C20 alkyl containing not more than four double bonds, phenyl, or naphthyl;

$R_2$ is hydroxyl, phenyl, C1–C5 alkoxy, or C1–C5 alkylthio;

$R_3$ is linear or branched, saturated or unsaturated C1–C20 alkyl containing not more than four double bonds, and is unsubstituted or substituted with one to three hydroxy groups;

$R_4$ is C1–C5 alkyl; or $R_3$ and $R_4$ are covalently joined and together with $N^+$ form a five or six membered monocyclic ring or with $N^+$ form a monocyclic ring which contains one further hetero atom selected form oxygen, nitrogen or sulfur and is unsubstituted or substituted from one to three times by hydroxy or C1–C4 alkylhydroxy;

$R_5$ is C1–C5 alkyl; and $Z^-$ is a pharmaceutically acceptable anion;

wherein the amount is effective to treat tumors, HIV infection or a condition associated with protein kinase C activity in a mammal.

4. A pharmaceutical composition according to claim 3, wherein $R_3$ is linear or branched, saturated or unsaturated C1–C18 alkyl containing not more than three double bonds, and which is substituted from zero to three times by hydroxy; wherein $R_4$ is methyl, ethyl, or propyl; or in the alternative $R_3$ and $R_4$ are covalently joined and together with $N^+$ form a monocyclic ring selected from the class consisting of piperidine, pyridine, morpholine, pyrrolidine, piperazine, thiazole, and imidazole, which ring is substituted from zero to three times by hydroxy or C1–C4 alkylhydroxy; and wherein $R_5$ is methyl, ethyl, or propyl, except that when either $R_3$ or $R_4$ is joined to $N^+$ with a double bond, then $R_5$ is absent.

5. A pharmaceutical composition according to claim 3, wherein Z⁻ is chlorine, bromine, or iodine.

6. A compound according to claim 1, wherein $R_8$ is hydrogen or C1–C8 linear alkyl.

7. A compound according to claim 1, wherein $R_9$ is saturated or unsaturated linear C1–C19 linear alkyl containing not more than three double bonds.

8. A compound according to claim 1, wherein Z⁻ is chlorine, bromine, or iodine.

9. A method of treating tumors in a subject in need of such treatment which comprises administering to the subject an effective amount of a compound of the formula:

$$R_1-X-R_2-N^+(R_3)(R_4)(R_5) \ Z^-$$

wherein $R_1$ is a linear C10–C20 alkyl containing not more than four double bonds, or C10–C20 alkylcarbonyl containing not more than four double bonds;

X is O or S;

$R_2$ is ethylene or n-propylene which is unsubstituted or is 2-substituted by hydroxyl, C1–C5 alkoxy, or C1–C5 alkylthio;

$R_3$ is linear or branched, saturated or unsaturated C1–C20 alkyl containing not more than four double bonds, and is unsubstituted or substituted from one to three times by hydroxy groups;

$R_4$ is C1–C5 alkyl;

or $R_3$ and $R_4$ are covalently joined and together with N⁺ form a five or six membered monocyclic ring or with N⁺ form a monocyclic ring which contains one further hetero atom selected from oxygen, nitrogen or sulfur and is unsubstituted or substituted from one to three times by hydroxy or C1–C4 alkylhydroxy;

$R_5$ is C1–C5 alkyl, except that when either $R_3$ or $R_4$ is joined to N⁺ with a double bond, then $R_5$ is absent; and Z⁻ is a pharmaceutically acceptable anion.

10. A method of claim 9, wherein $R_1$ is a linear C12–C18 alkyl containing not more than three double bonds.

11. A method according to claim 9, wherein $R_3$ is linear or branched, saturated or unsaturated C1–C18 alkyl containing not more than three double bonds, and which is substituted from one to three times by hydroxy; wherein $R_4$ is methyl, ethyl, or propyl; or in the alternative $R_3$ and $R_4$ are covalently joined and together with N⁺ form a monocyclic ring selected from the class consisting of piperidine, pyridine, morpholine, pyrrolidine, piperazine, thiazole, and imidazole, which ring is substituted from zero to three times by hydroxy or C1–C4 alkylhydroxy; and wherein $R_5$ is methyl, ethyl, or propyl, except that when either $R_3$ or $R_4$ is joined to N⁺ with a double bond, then $R_5$ is absent.

12. A method of claim 9, wherein Z⁻ is chlorine, bromine, or iodine.

13. A method of treating a condition associated with protein kinase C activity in a subject in need of such treatment, which comprises administering to the subject an effective amount of a compound of the formula:

$$\begin{array}{l} CH_2-X-R_1 \\ | \\ CH-R_2 \\ | \\ CH_2-N^+(R_3)(R_4)(R_5) \ Z^- \end{array}$$

wherein:

X is S or O;

$R_1$ is linear or branched, saturated or unsaturated C3–C20 alkyl containing not more than four double bonds;

linear or branched, saturated or unsaturated C3–C20 alkylcarbonyl containing not more than four double bonds; phenyl or naphthyl;

$R_2$ is H, hydroxyl, phenyl, C1–C5 alkylcarbonyloxy, C1–C5 alkylthio, C1–C5 alkylcarboximido, or C1–C5 alkoxy which is unsubstituted or is substituted by phenyl or C1–C5 alkoxy;

or wherein $R_1$, $R_2$ and X together are

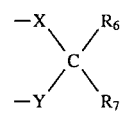

forming a five-membered monocyclic ring where $R_6$ is H or C1–C5 alkyl, $R_7$ is C1–C20 alkyl and Y is O or S;

$R_3$ is linear or branched, saturated or unsaturated C1–C20 alkyl containing not more than four double bonds, and is unsubstituted or substituted from one to three times by hydroxy groups;

$R_4$ is C1–C5 alkyl;

$R_5$ is C1–C5 alkyl;

Z⁻ is a pharmaceutically acceptable anion;

wherein said amount is effective to inhibit protein kinase C activity in the subject.

14. A method according to claim 13, wherein $R_1$ is C14–C20 linear saturated or unsaturated alkyl containing not more than three double bonds.

15. A method according to claim 13, wherein Z⁻ is chlorine, bromine, or iodine.

16. A method of treating an HIV-1 infection in a subject in need of such treatment, comprising administering said subject an amount effective to treat said infection of a compound of the formula:

$$R_1-X-R_2-N^+(R_3)(R_4)(R_5) \ Z^-$$

wherein:

X is S or O;

$R_1$ is linear or branched, saturated or unsaturated C10–C20 alkyl containing not more than four double bonds, linear or branched, saturated or unsaturated C10–C20 alkylcarbonyl containing not more than four double bonds, phenyl, or naphthyl;

$R_2$ is C5 to C6 cycloalkylene or a straight-chained or branched, saturated or unsaturated aliphatic hydrocarbon chain containing 2–8 carbon atoms, which is unsubstituted or substituted one or more times by hydroxyl, phenyl, C1–C5 alkylcarbonyloxy, C1–C5 alkylthio, C1–C5 alkylcarboxamido or by C1–C5 alkoxy which is unsubstituted or is substituted by phenyl or C1–C5 alkoxy; or $R_2$ is joined to X with

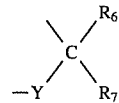

wherein Y is O or S and is joined to $R_2$ and $R_1$ is absent, to form a five-membered monocyclic ring where $R_6$ is H or C1–C5 alkyl, and $R_7$ is C1–C20 alkyl;

$R_3$ is a linear or branched, saturated or unsaturated C1–C20 alkyl containing not more than four double bonds, which is unsubstituted or substituted with one to three hydroxy groups;

$R_4$ is hydrogen or C1–C5 alkyl;

or $R_3$ and $R_4$ are covalently joined and together with $N^+$ form a five or six membered monocyclic ring selected from the group consisting of piperidine, pyridine, morpholine, pyrrolidine, piperazine, thiazole, and imidazole, and which is unsubstituted or substituted from one to three times by hydroxy or C1–C4 alkylhydroxy;

$R_5$ is hydrogen or C1–C5 alkyl; and $Z^-$ is a pharmaceutically acceptable anion.

17. A method according to claim 16, wherein $R_1$ is C14–C20 linear saturated or unsaturated alkyl containing not more than three double bonds.

18. A method according to claim 16, wherein $R_2$ is C2–C4 linear alkyl which is unsubstituted or is substituted one or two times by hydroxyl, phenyl, C1–C5 alkylcarbonyloxy, C1–C5 alkylthio, C1–C5 alkylcarboxamido or by C1–C5 alkoxy which is unsubstituted or is substituted by phenyl or C1–C5 alkoxy.

19. A method according to 16, claim wherein $R_3$ is linear or branched, saturated or unsaturated C1–C18 alkyl containing not more than three double bonds, and which is unsubstituted or substituted from one to three times by hydroxyl; wherein $R_4$ is methyl, ethyl, or propyl; or in the alternative $R_3$ and $R_4$ are covalently joined and together with $N^+$ form a monocyclic ring selected from the class consisting of piperidine, pyridine, morpholine, pyrrolidine, piperazine, thiazole, and imidazole, which ring is unsubstituted or substituted from one to three times by hydroxy or C1–C4 alkylhydroxy; and wherein $R_5$ is methyl, ethyl, or propyl.

20. A method according to claim 16, wherein $Z^-$ is chlorine, bromine, or iodine.

21. A method according to claim 16, wherein:

$R_1$ is C14–C20 linear saturated or unsaturated alkyl containing not more than three double bonds;

$R_2$ is C2–C4 linear alkyl which is unsubstituted or is substituted one or two times by hydroxyl, phenyl, C1–C5 alkylcarbonyloxy, C1–C5 alkylthio, C1–C5 alkylcarboxamido or by C1–C5 alkoxy which is unsubstituted or is substituted by phenyl or C1–C5 alkoxy;

$R_3$ is linear or branched, saturated or unsaturated C1–C18 alkyl containing not more than three double bonds, and which is unsubstituted or substituted from one to three times by hydroxy;

$R_4$ is methyl, ethyl, or propyl; or in the alternative $R_3$ and $R_4$ are covalently joined and together with $N^+$ form a five or six membered monocyclic ring selected from the class consisting of piperidine, pyridine, morpholine, pyrrolidine, piperazine, thiazole, and imidazole, which ring is unsubstituted or substituted from one to three times by hydroxy or C1–C4 alkylhydroxy; and $R_5$ is methyl, ethyl, or propyl.

22. A method according to claim 16, where said compound is selected from the group consisting of:

(±)-3-hexadecylthio-2-methoxy-N,N-dimethyl-N-β-hydroxyethyl-1-propyl ammonium bromide;

(±)-3-hexadecylthio-2-ethoxy-N,N-dimethyl-N-β-hydroxyethyl-1-propyl ammonium bromide; and (±)-3-octadecylthio-2-methoxy-N,N-dimethyl-N-gamma-hydroxypropyl-1-propyl ammonium bromide.

23. A method of treating an HIV-1 infection in a subject in need of such treatment, comprising administering to said subject in an amount effective to treat said infection a compound of the formula:

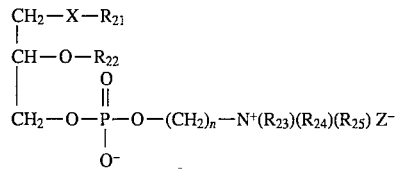

wherein:

n is 2–4;

X is S, O, or NHC(O);

$R_{21}$ is C14–C20 linear saturated or unsaturated alkyl containing not more than three double bonds;

$R_{22}$ is hydrogen, methyl, or ethyl;

$R_{23}$, $R_{24}$ and $R_{25}$ are independently either hydrogen or methyl; and $Z^-$ is a pharmaceutically acceptable anion.

24. The method according to claim 23, wherein X is NHC(O), $R_{21}$ is C17 linear saturated alkyl, $R_{22}$ is ethyl, n is 2, and $R_{23}$, $R_{24}$ and $R_{25}$ are each methyl.

25. A method of treating tumors, HIV-1 infection, or a condition associated with protein kinase C activity in a subject in need of such treatment which comprises administering to the subject an effective amount of a compound of the formula:

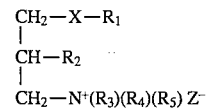

wherein:

X is S or NHC(O);

$R_1$ is linear or branched, saturated or unsaturated C14–C20 alkyl containing not more than four double bonds, phenyl, or naphthyl;

$R_2$ is hydrogen, hydroxyl, phenyl, C1–C5 alkoxy, or C1–C5 alkylthio;

$R_3$ is linear or branched, saturated or unsaturated C1–C20 alkyl containing not more than four double bonds, and is unsubstituted or substituted with one to three hydroxy groups;

$R_4$ is C1–C5 alkyl; or $R_3$ and $R_4$ are covalently joined and together with $N^+$ form a five or six membered monocyclic ring or with $N^+$ form a monocyclic ring which contains one further hetero atom selected form oxygen, nitrogen or sulfur and is unsubstituted or substituted from one to three times by hydroxy or C1–C4 alkylhydroxy;

$R_5$ is C1–C5 alkyl; and $Z^-$ is a pharmaceutically acceptable anion.

26. A method according to claim 25, wherein $R_3$ is linear or branched, saturated or unsaturated C1–C18 alkyl containing not more than three double bonds, and which is substituted from zero to three times by hydroxy; wherein $R_4$ is methyl, ethyl, or propyl; or in the alternative $R_3$ and $R_4$ are covalently joined and together with $N^+$ form a monocyclic ring selected from the class consisting of piperidine, pyridine, morpholine, pyrrolidine, piperazine, thiazole, and imidazole, which ring is substituted from zero to three times by hydroxy or C1–C4 alkylhydroxy; and wherein $R_5$ is methyl, ethyl, or propyl, except that when either $R_3$ or $R_4$ is joined to $N^+$ with a double bond, then $R_5$ is absent.

27. A method according to claim 25, wherein $Z^-$ is chlorine, bromine, or iodine.

28. A method of treating tumors, HIV-1 infection, or a condition associated with protein kinase C activity in a subject in need of such treatment which comprises administering to the subject an effective amount of a compound of the formula:

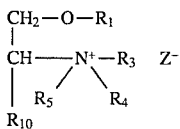

wherein:

$R_1$ is linear or branched, saturated or unsaturated C14–C20 alkyl containing not more than four double bonds, linear or branched, saturated or unsaturated C10–C20 alkylcarbonyl containing not more than four double bonds, phenyl, or naphthyl;

$R_3$ is linear or branched, saturated or unsaturated C2–C20 alkyl containing not more than four double bonds, is hydroxy substituted at the terminal carbon and is substituted with zero to two additional hydroxy groups;

$R_4$ is hydrogen or C1–C5 alkyl;

$R_5$ is hydrogen or C1–C5 alkyl;

$R_{10}$ is hydrogen or methyl; and $Z^-$ is a pharmaceutically acceptable anion.

29. A method according to claim 28, wherein $R_3$ is linear or branched, saturated or unsaturated C2–C10 alkyl containing not more than three double bonds, and which is hydroxy substituted at the terminal carbon and is substituted from zero to two additional hydroxy groups; wherein $R_4$ is methyl, ethyl, or propyl; and wherein $R_5$ is methyl, ethyl, or propyl.

30. A method according to claim 28, wherein $Z^-$ is chlorine, bromine, or iodine.

31. A method of treating tumors, HIV-1 infection, or a condition associated with protein kinase C activity in a subject in need of such treatment which comprises administering to the subject an effective amount of a compound of the formula:

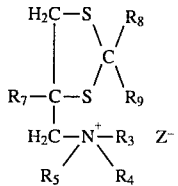

wherein:

$R_7$ is hydrogen, phenyl, or linear or branched, saturated or unsaturated C1–C16 alkyl containing not more than four double bonds or one triple bond;

$R_8$ is hydrogen or saturated or unsaturated, linear or branched C1–C5 alkyl;

$R_9$ is saturated or unsaturated, linear or branched C1–C19 alkyl containing not more than four double bonds;

$R_3$ is linear or branched, saturated or unsaturated C1–C20 alkyl containing not more than four double bonds, is hydroxy substituted at the terminal carbon and is substituted with zero to three additional hydroxy groups;

$R_4$ is C1–C5 alkyl;

$R_5$ is C1–C5 alkyl; and $Z^-$ is a pharmaceutically acceptable anion.

32. A method according to claim 31, wherein $R_8$ is hydrogen or C1–C8 linear alkyl.

33. A method according to claim 31, wherein $R_9$ is saturated or unsaturated linear C1–C19 linear alkyl containing not more than three double bonds.

34. A method according to claim 31, wherein $R_3$ is linear or branched, saturated or unsaturated C1–C18 alkyl containing not more than three double bonds, and which is substituted with one to three hydroxy groups; wherein $R_4$ is methyl, ethyl, or propyl; and wherein $R_5$ is methyl, ethyl, or propyl.

35. A method according to claim 31, wherein $Z^-$ is chlorine, bromine, or iodine.

36. A method of treating tumors, HIV-1 infection, or a condition associated with protein kinase C activity in a subject in need of such treatment which comprises administering to the subject an effective amount of a compound of the formula

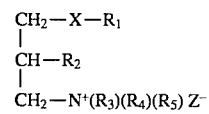

wherein:

$R_1$ is C10–C20 linear saturated or unsaturated alkyl containing not more than one double bond;

$R_2$ is H or C1–C5 alkoxy;

X is S or O;

$R_3$ and $R_4$ are covalently joined and together with $N^+$ form a five or six membered monocyclic ring selected from the class consisting of piperidine, pyridine, morpholine, pyrrolidine, piperazine, thiazole, and imidazole, which ring is substituted with zero to three hydroxy groups or and substituted with zero to three C1–C4 alkylhydroxy groups; $R_5$ is H or C1–C5 alkyl; and $Z^-$ is a pharmaceutically acceptable anion.

37. A method of claim 36, wherein $Z^-$ is chlorine, bromine, or iodine.

38. A method according to claim 23, wherein n is 2.

39. A method according to claim 23, wherein $R_{21}$ is C16–C18 linear alkyl containing not more than one double bond.

40. A method according to claim 23, wherein $R_{23}$, $R_{24}$ and $R_{25}$ are methyl.

* * * * *

UNITED STATES PATENT AND TRADEMARK OFFICE
CERTIFICATE OF CORRECTION

PATENT NO.   :   5,614,548

DATED        :   March 25, 1997

INVENTOR(S)  :   Claude Piantadosi et al.

It is certified that error appears in the above-identified patent and that said Letters Patent is hereby corrected as shown below:

In Column 3, line 54, "$R_1$" should read --$R_7$--.

In Column 7, line 56, "-N-6-" should read --N-δ---.

In Column 16, line 18, "(m, 2H, S-$CH_2$)" should read --(m, 2H, S-$\underline{CH}_2$)--.

In Column 20, line 59, in Table 1, "losted" should read --tested--.

In Column 21, line 66, "2-Phenoxy" should read --2-phenoxy--.

In Column 24, line 55, Table 3, "cell" should read --cells--.

In Column 25, line 43, "1 x 106" should read --1 x $10^6$--.

In Column 25, line 24, Table 4, "Lanes" should read --Lines--.

In Column 28, line 6, "($IC_{50}$32 0.6μM)" should read --($IC_{50}$=0.6μM)--.

UNITED STATES PATENT AND TRADEMARK OFFICE
CERTIFICATE OF CORRECTION

PATENT NO. : 5,614,548

DATED : March 25, 1997

INVENTOR(S) : Claude Piantadosi et al.

It is certified that error appears in the above-indentified patent and that said Letters Patent is hereby corrected as shown below:

In Column 29, line 54, "$R_2$" should read --$R_8$--.

Signed and Sealed this

Eighteenth Day of November 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO     5,614,548
DATED     March 25, 1997
INVENTOR(S)     Claude Piantadosi et al It is certified that error appears in the above identified patent and that said Letters Patent is hereby corrected as shown below On Title Page [73], Assignee please add --The University of North Carolina at Chapel Hill, County of Orange, North Carolina--

Signed and Sealed this

Third Day of February, 1998

*Attest:*

BRUCE LEHMAN

*Attesting Officer*      *Commissioner of Patents and Trademarks*